(12) United States Patent
Wilson et al.

(10) Patent No.: US 9,770,011 B2
(45) Date of Patent: Sep. 26, 2017

(54) VETERINARY COMPOSITION AND METHODS FOR NON-SURGICAL NEUTERING AND CASTRATION

(71) Applicant: The Trustees of The University of Pennsylvania, Philadelphia, PA (US)

(72) Inventors: James M. Wilson, Glen Mills, PA (US); Christian Hinderer, Philadelphia, PA (US); John F. Wilson, Washington, MI (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/431,347

(22) PCT Filed: Sep. 27, 2013

(86) PCT No.: PCT/US2013/062078
§ 371 (c)(1),
(2) Date: Mar. 26, 2015

(87) PCT Pub. No.: WO2014/052693
PCT Pub. Date: Apr. 3, 2014

(65) Prior Publication Data
US 2015/0230430 A1 Aug. 20, 2015

Related U.S. Application Data

(60) Provisional application No. 61/785,547, filed on Mar. 14, 2013, provisional application No. 61/707,900, filed on Sep. 29, 2012.

(51) Int. Cl.
| | | |
|---|---|---|
| *C12N 15/00* | (2006.01) | |
| *C07K 16/00* | (2006.01) | |
| *A01K 21/00* | (2006.01) | |
| *A61K 31/713* | (2006.01) | |
| *C07K 16/26* | (2006.01) | |
| *A61K 9/19* | (2006.01) | |
| *A01K 29/00* | (2006.01) | |

(52) U.S. Cl.
CPC .............. *A01K 21/00* (2013.01); *A01K 29/00* (2013.01); *A61K 9/19* (2013.01); *A61K 31/713* (2013.01); *C07K 16/26* (2013.01)

(58) Field of Classification Search
None
See application file for complete search history.

(56) References Cited

U.S. PATENT DOCUMENTS

| | | | |
|---|---|---|---|
| 4,676,981 A | 6/1987 | Silversides | |
| 4,879,112 A | 11/1989 | Silversides et al. | |
| 6,303,123 B1 | 10/2001 | Grimes et al. | |
| 6,660,514 B1 | 12/2003 | Zolotukhin et al. | |
| 2002/0086847 A1* | 7/2002 | Chain | C07K 16/18 514/44 R |
| 2003/0223966 A1* | 12/2003 | Fraites, Jr. | A61K 38/47 424/93.2 |
| 2005/0239701 A1 | 10/2005 | Baker et al. | |
| 2006/0166318 A1 | 7/2006 | Lockert et al. | |
| 2009/0035327 A1 | 2/2009 | Clark et al. | |
| 2011/0165189 A1 | 7/2011 | Wu et al. | |
| 2013/0034552 A1* | 2/2013 | Chaikof | A61K 47/48246 424/134.1 |
| 2014/0223591 A1 | 8/2014 | Hay | |
| 2015/0010578 A1 | 1/2015 | Balazs | |

FOREIGN PATENT DOCUMENTS

| | | |
|---|---|---|
| WO | WO-92/12733 | 8/1992 |
| WO | WO-00/29443 A1 | 5/2000 |
| WO | WO-2010/042562 | 4/2010 |
| WO | WO-2014/120975 | 8/2014 |

OTHER PUBLICATIONS

Lock, Hum Gene Ther 2010;21:1259-71.*
Naz, Contraceptive Vaccines, Drugs, 65(5):593-603 (2005).
Naz, Recent advances in contraceptive vaccine development: a mini-review, Human Reproduction, 20(12):3271-3283 (2005).
Levy et al, Long-term fertility control in female cats with GonaCon, a GnRH immunocontraceptive 76(8):1517-1525 (2011).
Fraser, Antifertility effects of GnRH J. Reprod. Fert. 64:503-515 (1982).
Balazs et al., Antibody-based protection against HIV infection by vectored immunoprophylaxis, Nature, 481:81-84 (2012) and Supplementary Information (Materials and Methods pp. 1-2).
Silversides et al. Monoclonal Antibodies Against LHRH: Development and Immunoactivity in Vivo and in Vitro (ABSTRACT). Journal of Reproductive Immunology, vol. 7(2):171-184, Feb. 1985.
Manno et al. AAV-mediated factor IX gene transfer to skeletal muscle in patients with severe hemophilia B. Blood. vol. 101(8):2963-2972, Dec. 19, 2002.
Meeusen et al. Current Status of Veterinary Vaccines. Clinical Microbiology Reviews, vol. 20(3):489-510, Jul. 2007.
Johnson et al. Vector-mediated gene transfer engenders long-lived neutralizing activity and protection against SIV infection in monkeys. Nature Medicine. vol. 15(8):901-907, Aug. 2009.
Jung et al. Induction of castration by immunization of male dogs with recombinant gonadotropin-releasing hormone (GnRH)-canine distemper virus (CDV) T helper cell epitope p. 35. Journal of Veterinary Science. vol. 6(1):21-24, Mar. 31, 2005.
Talwar et al. Bioeffective monoclonal antibody against the decapeptide gonadotropin-releasing hormone: Reacting deteiminant and action on ovulation and estrus suppression. PNAS. vol. 82:1228-1231, Feb. 1985.

(Continued)

*Primary Examiner* — Janice Li
(74) *Attorney, Agent, or Firm* — Howson & Howson LLP; Cathy A. Kodroff

(57) ABSTRACT

A method for non-surgical neutering or castration of a non-human mammal for AAV-mediated delivery of an anti-GnRH polypeptide to a non-human animal is described. More particularly, the animal is administered an adeno-associated virus (AAV) vector having an AAV capsid having packaged therein nucleic acid sequences comprising an AAV 5' inverted terminal repeat (ITR), a sequence encoding a polypeptide which specifically binds gonadotropin releasing hormone (GnRH) under control of regulatory sequences which direct expression of the polypeptide, and an AAV 3' ITR. A composition comprising the AAV-anti-GnRH may also be used for inhibiting tumor growth in a mammal with a cancer responsive to gonadal steroid hormones.

20 Claims, 5 Drawing Sheets

(56) References Cited

OTHER PUBLICATIONS

Sabatino et al. Efficacy and Safety of Long-term Prophylaxis in Severe Hemophilia a Dogs Following Liver Gene Therapy Using AAV Vectors. Molecular Therapy. vol. 19(3):442-449, Mar. 2011.
Urbanski et al. Monoclonal antibodies to luteinizing hormone releasing hormone-production, characterization, and immunocytochemical application. Biology of Reproduction. vol. 44: 681-686, Apr. 1, 1991.
Wang et al. Sustained correction of disease in naive and AAV2-pretreated hemophilia B dogs: AAV2/8-mediated, liver-directed gene therapy. Blood. vol. 105(8):3079-3086, Apr. 15, 2005.
Bell et al. Evaluation of Adeno-Associated Viral Vectors for Liver-Directed Gene Transfer in Dogs. Human Gene Therapy. vol. 22(8):985-997. Aug. 2011.
International Search Report issued for priority International Patent Application No. PCT/US2013/062078, dated Apr. 4, 2014.
Written Opinion of the International Searching Authority issued for priority International Patent Application No. PCT/US2013/062078, dated Apr. 4, 2014.
Naz et al., Passive immunization for immunocontraception: lessons learned from infectious diseases, Frontiers in Bioscience (Landmark Edition), vol. 9(1):2457-2465, Sep. 2004.
Munks, Progress in Development of Immunocontraceptive Vaccines for Permanent Non-surgical Sterilization of Cats and Dogs, Reproduction in Domestic Animals, vol. 47: 223-227, Aug. 2012.
Bakker et al., Therapeutic Antibody Gene Transfer: An Active Approach to Passive Immunity, Molecular Therapy, vol. 10(3):411-416, Sep. 2004.
Supplementary European Search Report issued on European Patent Application No. 13842169, dated Apr. 18, 2016.
Communication dated May 18, 2016 issued on European Patent Application No. 13842169.

\* cited by examiner

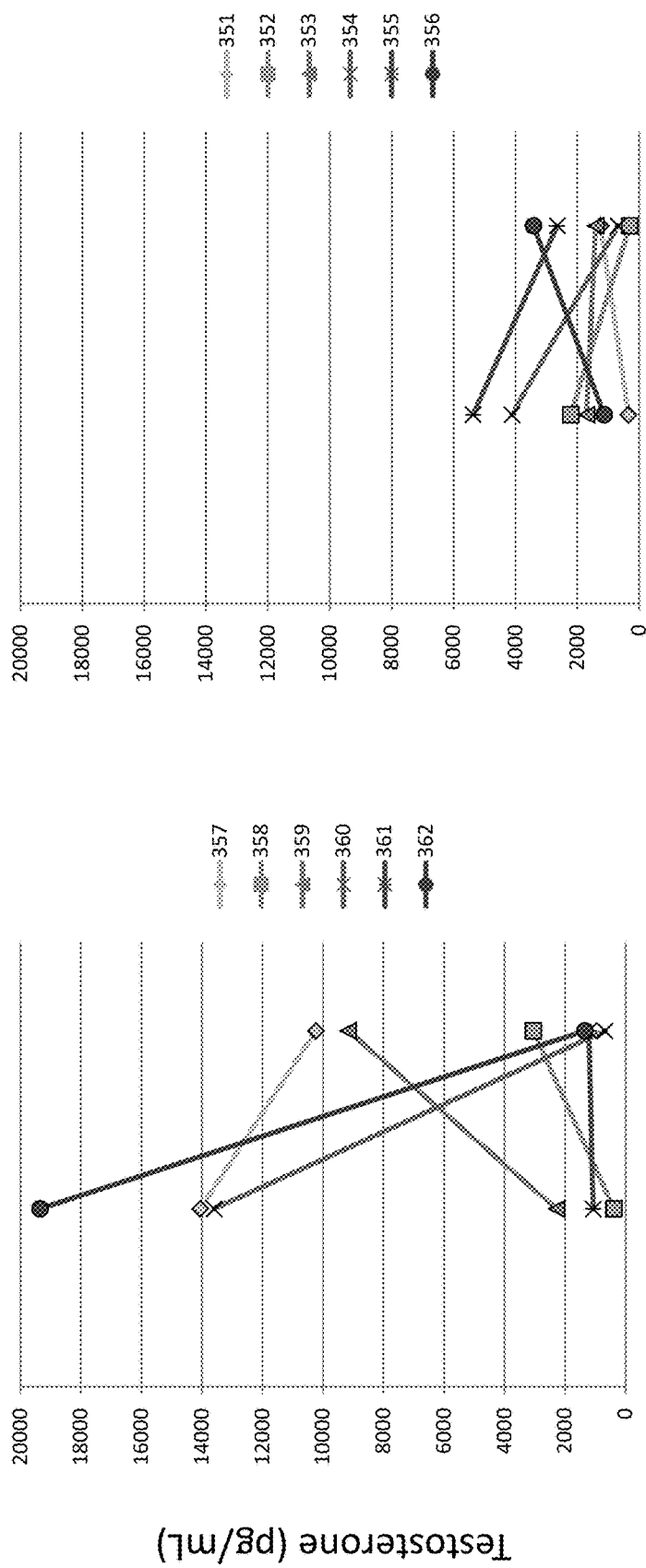

SEQUENCE LISTING

```
<160> NUMBER OF SEQ ID NOS: 34

<210> SEQ ID NO 1
<211> LENGTH: 10
<212> TYPE: PRT
<213> ORGANISM: Homo sapiens

<400> SEQUENCE: 1

Glu His Trp Ser Tyr Gly Leu Arg Pro Gly
1               5                   10

<210> SEQ ID NO 2
<211> LENGTH: 10
<212> TYPE: PRT
<213> ORGANISM: Gallus gallus

<400> SEQUENCE: 2

Glu His Trp Ser His Gly Trp Tyr Pro Gly
1               5                   10

<210> SEQ ID NO 3
<211> LENGTH: 10
<212> TYPE: PRT
<213> ORGANISM: Salmo salar

<400> SEQUENCE: 3

Glu His Trp Ser Tyr Gly Trp Leu Pro Gly
1               5                   10

<210> SEQ ID NO 4
<211> LENGTH: 10
<212> TYPE: PRT
<213> ORGANISM: Petromyzon marinus

<400> SEQUENCE: 4

Glu His Tyr Ser Leu Glu Trp Lys Pro Gly
1               5                   10

<210> SEQ ID NO 5
<211> LENGTH: 10
<212> TYPE: PRT
<213> ORGANISM: Petromyzon marinus
```

<400> SEQUENCE: 5

Glu His Trp Ser His Asp Trp Lys Pro Gly
1               5                   10

<210> SEQ ID NO 6
<211> LENGTH: 107
<212> TYPE: PRT
<213> ORGANISM: Mus musculus

<400> SEQUENCE: 6

Gln Ile Val Leu Thr Gln Ser Pro Ala Ile Met Ser Ala Ser Pro Gly
1               5                   10                  15

Glu Lys Val Thr Ile Thr Cys Ser Ala Thr Ser Ser Val Ser Tyr Ile
                20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Pro Thr
                85                  90                  95

Phe Gly Gly Gly Thr Lys Leu Glu Ile Lys Arg
            100                 105

<210> SEQ ID NO 7
<211> LENGTH: 682
<212> TYPE: DNA
<213> ORGANISM: Mus musculus

<400> SEQUENCE: 7
caaattgttc tcacccagtc tccagccatc atgtctgcat ctccagggga gaaggtcacc     60
ataacctgca gtgccactca agtgtaagtt acatacactg gttccagcag aagccaggca    120
cttctcccaa actctggatt tatagcacat ccaacctggc ttctggagtc cctgttcgct    180
tcagtggcag tggatctggg acctcttact ctctcacaat cagccgaatg gaggctgaag    240
atgctgccac ttattactgc cagcaaagga gtagttaccc acccacgttc ggagggggga    300
ccaactggaa ataaaacgvh cagatccagt tggtgcagtc tggacctgaa ctgaagaagc    360
ctggagagac agtcaagatc tcctgcaagg cttctggata tcccttcaca aactatggaa    420
tgaactgggt gaagcaggct ccaggaaagg gtttaaagtg gatgggctgg ataaacacct    480
acactggaga gccagcatgt gctgatgact tcaggggacg gtttgccatc tctttggaaa    540
cctccgccag actgcctatt tgcagatcaa caacctcata aatgaggaca cggcaacata    600
tttctgtgca agaacggggg gtggtaggta caactatggt atggactatt ggggtcaagg    660
aacctcagtc accgtctcct ca                                              682

<210> SEQ ID NO 8
<211> LENGTH: 107
<212> TYPE: PRT
<213> ORGANISM: Canis familiaris

<400> SEQUENCE: 8

Asp Ile Val Met Thr Gln Thr Pro Leu Ser Leu Ser Val Ser Pro Gly
1               5                   10                  15

Glu Pro Ala Ser Ile Ser Cys Ser Ala Thr Ser Ser Val Ser Tyr Ile
                20                  25                  30

```
His Trp Tyr Leu Gln Lys Ala Gly Gln Ser Pro Arg Leu Leu Pro Glu
            35                  40                  45

Ser Thr Ser Asn Leu Ala Ser Gly Val Pro Val Arg Phe Ser Gly Ser
    50                  55                  60

Gly Ser Gly Thr Asp Phe Thr Leu Arg Ile Gly Arg Val Glu Ala Glu
65                  70                  75                  80

Asp Ala Gly Ile Tyr Tyr Cys Gln Gln Arg Ser Ser Tyr Pro Pro Thr
                85                  90                  95

Phe Gly Gln Gly Thr Arg Leu Glu Val Arg Arg
                100                 105
```

<210> SEQ ID NO 9
<211> LENGTH: 636
<212> TYPE: DNA
<213> ORGANISM: Canis familiaris

<400> SEQUENCE: 9

```
gatatagtga tgacccaaac ccctctaagc ctatctgtct ccctggggga gccggcgagt      60
atcagctgca gcgccaccag cagcgtgtca tatatccact ggtacctgca aaaggctgga    120
cagtccccta gacttctgcc cgaaagcaca tctaacctgg ccagcggggt ccctgtgagg    180
tttagtggga gtgggagtgg caccgatttc accctccgaa ttggaagggt ggaggccgaa    240
gatgctggaa tctattactg tcagcaaaga agcagctacc ccctacctt cgggcagggc     300
accagacttg aggtccgcag gaatgatgct cagcctgctg tgtacctttt tcaaccaagc    360
cctgaccaac tgcataccgg cagtgcctct gtggtctgcc tgcttaatag cttctatccc    420
aaggacatta atgtgaagtg aaggttgac ggcgtgatac aggataccgg aattcaggaa     480
agtgtgacag aacaagataa ggatagcacc tatagcctgt ctagcaccct caccatgagc    540
agcacagagt acttgagtca tgagctgtat agctgtgaga ttacccacaa gagtctgcca    600
agcacccctta taaaaagttt ccagcgatct gagtgt                             636
```

<210> SEQ ID NO 10
<211> LENGTH: 107
<212> TYPE: PRT
<213> ORGANISM: Felis catus

<400> SEQUENCE: 10

```
Asp Ile Val Met Thr Gln Thr Pro Leu Ser Leu Ser Val Thr Pro Gly
1               5                   10                  15

Glu Pro Ala Ser Ile Ser Cys Ser Ala Thr Ser Ser Val Ser Tyr Ile
            20                  25                  30

His Trp Tyr Leu Gln Lys Pro Gly Gln Ser Pro Arg Arg Leu Ile Tyr
            35                  40                  45

Ser Thr Ser Asn Leu Ala Ser Gly Val Pro Val Arg Phe Ser Gly Ser
    50                  55                  60

Gly Ser Gly Thr Asp Phe Thr Leu Arg Ile Ser Arg Val Glu Ala Asp
65                  70                  75                  80

Asp Val Gly Val Tyr Tyr Cys Gln Gln Arg Ser Ser Tyr Pro Pro Thr
                85                  90                  95

Phe Gly Pro Gly Thr Lys Leu Glu Ile Lys Arg
                100                 105
```

<210> SEQ ID NO 11
<211> LENGTH: 648
<212> TYPE: DNA

<213> ORGANISM: Felis catus

<400> SEQUENCE: 11

| | |
|---|---|
| gacatcgtga tgacccaaac ccctctgagc ctgtccgtca ccccggggga gcccgccagc | 60 |
| ataagctgct ccgctaccag ctccgttagc tacattcact ggtatctgca aaagcctggc | 120 |
| cagagcccta ggcgactgat ctatagcacc tccaacctgg cctctggtgt gccagtgcgc | 180 |
| ttctctgggt ctggcagcgg gaccgacttt accctgagga ctccagagt ggaggctgat | 240 |
| gatgtggggg tgtactactg ccagcagagg agcagctatc ctcctacctt tggccccggc | 300 |
| accaagctgg agataaagag gagtgatgcc cagcccagcg tgtttctgtt ccaaccttct | 360 |
| ctggatgagc tgcacaccgg gagcgcctct atagtgtgta ttctgaatga tttctatccc | 420 |
| aaagaagtta atgtcaagtg gaaggtggat ggggtggtcc agaacaaggg catccaggaa | 480 |
| agcacgaccg aacagaactc caaggactcc acatattctc tgagtagtac cctgaccatg | 540 |
| agtagcaccg aataccagag tcacgagaaa ttcagctgcg aggtgaccca caagagcttg | 600 |
| gccagcaccc tagtgaagag ctttaaccga agcgagtgcc agcgagaa | 648 |

<210> SEQ ID NO 12
<211> LENGTH: 121
<212> TYPE: PRT
<213> ORGANISM: Mus musculus

<400> SEQUENCE: 12

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Pro Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Ala Cys Ala Asp Asp Phe
    50                  55                  60

Arg Gly Arg Phe Ala Ile Ser Leu Glu Thr Ser Ala Arg Thr Ala Tyr
65                  70                  75                  80

Leu Gln Ile Asn Asn Leu Ile Asn Glu Asp Thr Ala Thr Tyr Phe Cys
            85                  90                  95

Ala Arg Thr Gly Gly Gly Arg Tyr Asn Tyr Gly Met Asp Tyr Trp Gly
            100                 105                 110

Gln Gly Thr Ser Val Thr Val Ser Ser
        115                 120

<210> SEQ ID NO 13
<211> LENGTH: 363
<212> TYPE: DNA
<213> ORGANISM: Mus musculus

<400> SEQUENCE: 13

| | |
|---|---|
| cagatccagt tggtgcagtc tggacctgaa ctgaagaagc ctggagagac agtcaagatc | 60 |
| tcctgcaagg cttctggata cccttcaca aactatggaa tgaactgggt gaagcaggct | 120 |
| ccaggaaagg gtttaaagtg gatgggctgg ataaacacct acactggaga gccagcatgt | 180 |
| gctgatgact caggggacg gtttgccatc tctttggaaa cctccgccag aactgcctat | 240 |
| ttgcagatca caaacctcat aaatgaggac acggcaacat atttctgtgc aagaacgggg | 300 |
| ggtggtaggt acaactatgg tatggactat tggggtcaag gaacctcagt caccgtctcc | 360 |
| tca | 363 |

<210> SEQ ID NO 14
<211> LENGTH: 121
<212> TYPE: PRT
<213> ORGANISM: Canis familiaris

<400> SEQUENCE: 14

Glu Val Gln Leu Val Glu Ser Gly Gly Asp Leu Val Lys Pro Ala Gly
1               5                   10                  15

Ser Leu Arg Leu Ser Cys Val Ala Ser Gly Tyr Pro Phe Thr Asn Tyr
            20                  25                  30

Gly Met Asn Trp Val Arg Gln Ala Pro Gly Lys Gly Leu Gln Trp Val
        35                  40                  45

Ala Trp Ile Asn Thr Tyr Thr Gly Glu Pro Ala Cys Ala Asp Asp Phe
    50                  55                  60

Arg Gly Arg Phe Thr Ile Ser Arg Asp Asn Ala Lys Arg Thr Leu Tyr
65                  70                  75                  80

Leu Gln Met Asn Ser Leu Ile Ala Glu Asp Thr Ala Val Tyr Tyr Cys
                85                  90                  95

Ala Lys Thr Gly Gly Gly Arg Tyr Asn Tyr Gly Met Asp Tyr Trp Gly
            100                 105                 110

His Gly Thr Ser Leu Phe Val Ser Ser
        115                 120

<210> SEQ ID NO 15
<211> LENGTH: 1356
<212> TYPE: DNA
<213> ORGANISM: Canis familiaris

<400> SEQUENCE: 15
gaggtgcagc tggtggagag cggcggggat ctggtcaagc ctgccggcag cctgagactg      60
agctgcgtgg caagcggcta ccccttcaca aattatggca tgaactgggt gcgacaggcc     120
cctggcaagg gcctgcagtg ggtggcctgg ataaacacct acaccgggga accagcatgt     180
gcagatgact tcagaggccg cttcaccata tctcgagaca atgctaagcg acccctgtat     240
ctgcagatga actcactgat tgcagaggac acagcagtgt actactgtgc caagacagga     300
ggagggcgct acaactatgg catggactac tggggccacg gaacgagcct gtttgtctca     360
tctgcgtcga ccacagcccc ctctgtgttc ccctggccc cttcctgtgg gtcaacctct     420
ggcagcacag tggccctggc gtgtcttgtg tctggctact ccctgaacc tgtgacagtc     480 agctggaaca gcggaagcct gacctctgga gtgcacacct ccccagtgt cctgcaaagc     540 tcaggcctgc acagcctgtc aagtatggtg acagtgccca gtagcaggtg gccttctgaa     600
acctttacct gcaacgtggt gcaccctgca tccaacacca agtggataa gcctgttttc     660 aatgagtgca gatgcacaga tacacctccc tgccctgtgc ctgagcctct gggaggacca     720
tcagtcctga tcttccctcc aaagcctaag gatatcctgc ggatcaccag aaccccgag     780 gtcacctgtg tcgtcctgga tctgggccgg aagatcctg aagtgcagat tagctggttt     840
gtggacggca aggaagtgca cacagctaag acccaatccc gggagcagca gttcaatggc     900
acctaccggg tggtctctgt cctgcccatc gagcaccaag attggctgac aggcaaagag     960
tttaagtgcc gagtcaacca catagatctt ccctccccta ttgagcggac catctccaag    1020
gcacgggggc gagcgcacaa accctctgtc tatgtgctgc ctccctctcc caaagaattg    1080
agctctagcg atacagtgtc aatcacctgc ctgatcaagg acttctaccc ccctgacatt    1140

```
gatgttgaat ggcaatcaaa tgggcagcaa gaaccagaga gaaaacacag aatgacccct      1200
ccacagctgg atgaggacgg gtcctacttt ctgtactcta aactttccgt ggacaagagc      1260
agatggcagc agggagaccc tttcacctgt gcggtcatgc acgagacact gcaaaaccac      1320
tacacagatc tgtccttgag ccactcacct ggcaag                                1356
```

<210> SEQ ID NO 16
<211> LENGTH: 121
<212> TYPE: PRT
<213> ORGANISM: Felis catus

<400> SEQUENCE: 16

```
Asp Val Gln Leu Met Glu Ser Gly Gly Asp Leu Val Lys Pro Gly Gly
1               5                   10                  15

Ser Leu Arg Leu Thr Cys Val Ala Ser Gly Tyr Pro Phe Thr Asn Tyr
            20                  25                  30

Gly Met Asn Trp Val Arg Gln Ala Pro Gly Lys Gly Leu Gln Trp Val
        35                  40                  45

Ala Trp Ile Asn Thr Tyr Thr Gly Glu Pro Ala Cys Ala Asp Asp Phe
    50                  55                  60

Arg Gly Arg Phe Thr Ile Ser Arg Asp Asn Ala Lys Arg Thr Leu Tyr
65                  70                  75                  80

Leu Gln Met Asn Ser Leu Ile Thr Glu Asp Thr Ala Thr Tyr Tyr Cys
                85                  90                  95

Thr Arg Thr Gly Gly Gly Arg Tyr Asn Tyr Gly Met Asp Tyr Trp Gly
            100                 105                 110

Gln Gly Ala Leu Val Thr Val Ser Ser
        115                 120
```

<210> SEQ ID NO 17
<211> LENGTH: 1367
<212> TYPE: DNA
<213> ORGANISM: Felis catus

<400> SEQUENCE: 17

```
acgtgcagct gatggagtct gggggcgacc tagtcaagcc tgggggtcc  ctgcggctta       60 cgtgtgtggc aagtgggtac cccttcacca actatggaat gaactgggtc agacaggccc      120
ctggaaaagg cctgcagtgg gtggcctgga tcaacaccta caggagaa  cctgcctgtg       180 cagatgactt tagaggccga ttcaccattt caagagataa cgcgaagcga accttgtact      240
tacagatgaa ctccctgatc acagaagaca cagcaaccta ctactgtacc ggacaggag       300 ggggccgcta caactatggc atggactact ggggcaagg  agcactggtg acagtctcat      360
ctgcgtcgac cacagccccc tctgtgttcc cctggcccc  ttcttgtgga accacctctg      420
gagcgacagt ggctctggcg tgccttgtcc tgggtactt  ccctgaacct gtgaccgtca      480
gctggaactc cggagcactg acatctggag tgcacacctt cctgcggtc  ctgcaagctt      540 ccggcctgta ctcactgtcc agcatggtga ctgtgccttc ttcaagatgg ctgtctgaca      600
cgttcacctg caatgtggcg caccctcctt caaacacaaa ggtcgataag accgtgagaa      660
agacagacca cccccctggc caaagccct  gcgactgtcc taagtgcccc cctcctgaaa      720
tgctgggcgg ccccagcatc ttcatattcc cccctaagcc caagacacc  ttgagtatct      780 ctcgaacacc agaagtcacc tgcctggtgg tggacctagg ccctgatgac tctgatgtgc      840
aaataacctg gttcgtggac aacacccagg tgtacaccgc caaaacctcc ccaagagagg      900
agcagttcaa ctccacctat cgggtcgtta gtgtgctgcc cattctgcac caagactggc      960
```

```
tgaaaggcaa ggagttcaag tgcaaggtca atagcaaatc actgccctct cccattgaaa    1020
gaaccattag caaggccaag ggacagcccc acgaacctca ggtgtatgtg ctgccacctg    1080
cccaggaaga gctcagccgc aacaaggtct ctgtgacctg cctgatcaag tccttccacc    1140
ctcctgacat agcagtggag tgggaaataa caggacagcc tgagcctgaa acaactacc     1200 gcaccacccc tccccaactg gactccgatg gaacctactt tgtctactct aagctgtctg    1260
tggatcgaag ccactggcaa aggggcaaca cctacacctg ctctgtcagc cacgaagccc    1320
tgcacagcca ccacacccaa aagtccctga cccagagccc cggaaag                  1367
```

<210> SEQ ID NO 18
<211> LENGTH: 10
<212> TYPE: PRT
<213> ORGANISM: Artificial sequence
<220> FEATURE:
<223> OTHER INFORMATION: Antibody CDR VH1
<220> FEATURE:
<221> NAME/KEY: PEPTIDE
<222> LOCATION: (1)..(10)

<400> SEQUENCE: 18

Gly Tyr Pro Phe Thr Asn Tyr Gly Met Asn
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Antibody CDR VH1
<220> FEATURE:
<221> NAME/KEY: Peptide
<222> LOCATION: (1)..(7)

<400> SEQUENCE: 19

Gly Tyr Pro Phe Thr Asn Tyr
1               5

<210> SEQ ID NO 20
<211> LENGTH: 5
<212> TYPE: PRT
<213> ORGANISM: Artificial Sequence
<220> FEATURE:
<223> OTHER INFORMATION: Antibody CDR VH1
<220> FEATURE:
<221> NAME/KEY: PEPTIDE
<222> LOCATION: (1)..(5)

<400> SEQUENCE: 20

Asn Tyr Gly Met Asn
1               5

<210> SEQ ID NO 21
<211> LENGTH: 19
<212> TYPE: PRT
<213> ORGANISM: Artificial Sequence
<220> FEATURE:
<223> OTHER INFORMATION: Antibody CDR VH2
<220> FEATURE:
<221> NAME/KEY: Peptide
<222> LOCATION: (1)..(19)

<400> SEQUENCE: 21

Trp Ile Asn Thr Tyr Thr Gly Glu Pro Ala Cys Ala Asp Asp Phe Arg
1               5                   10                  15

Gly Arg Phe

<210> SEQ ID NO 22
<211> LENGTH: 12
<212> TYPE: PRT
<213> ORGANISM: Artificial Sequence
<220> FEATURE:
<223> OTHER INFORMATION: Antibody CDR VH2
<220> FEATURE:
<221> NAME/KEY: Peptide
<222> LOCATION: (1)..(12)

<400> SEQUENCE: 22

Trp Ile Asn Thr Tyr Thr Gly Glu Pro Ala Cys Ala
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Antibody CDR VH3
<220> FEATURE:
<221> NAME/KEY: Peptide
<222> LOCATION: (1)..(12)

<400> SEQUENCE: 23

Thr Gly Gly Gly Arg Tyr Asn Tyr Gly Met Asp Tyr
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Antibody CDR VL1
<220> FEATURE:
<221> NAME/KEY: Peptides
<222> LOCATION: (1)..(10)

<400> SEQUENCE: 24

Ser Ala Thr Ser Ser Val Ser Tyr Ile His
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Antibody CDR VL2
<220> FEATURE:
<221> NAME/KEY: Peptide
<222> LOCATION: (1)..(7)

<400> SEQUENCE: 25

Ser Thr Ser Asn Leu Ala Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Antibody CDR VL3
<220> FEATURE:
<221> NAME/KEY: Peptide
<222> LOCATION: (1)..(9)

<400> SEQUENCE: 26

Gln Gln Arg Ser Ser Tyr Pro Pro Thr
1               5

<210> SEQ ID NO 27
<211> LENGTH: 1356
<212> TYPE: DNA
<213> ORGANISM: Artificial Sequence
<220> FEATURE:
<223> OTHER INFORMATION: Full length antibody heavy chain (HC) with
      canine CDR coding sequence
<220> FEATURE:
<221> NAME/KEY: CDS
<222> LOCATION: (1)..(1356)

<400> SEQUENCE: 27

```
gag gtg cag ctg gtg gag agc ggc ggg gat ctg gtc aag cct gcc ggc      48
Glu Val Gln Leu Val Glu Ser Gly Gly Asp Leu Val Lys Pro Ala Gly
1               5                   10                  15 agc ctg aga ctg agc tgc gtg gca agc ggc tac ccc ttc aca aat tat      96
Ser Leu Arg Leu Ser Cys Val Ala Ser Gly Tyr Pro Phe Thr Asn Tyr
            20                  25                  30 ggc atg aac tgg gtg cga cag gcc cct ggc aag ggc ctg cag tgg gtg     144
Gly Met Asn Trp Val Arg Gln Ala Pro Gly Lys Gly Leu Gln Trp Val
        35                  40                  45 gcc tgg ata aac acc tac acc ggg gaa cca gca tgt gca gat gac ttc     192
Ala Trp Ile Asn Thr Tyr Thr Gly Glu Pro Ala Cys Ala Asp Asp Phe
    50                  55                  60 aga ggc cgc ttc acc ata tct cga gac aat gct aag cgg acc ctg tat     240
Arg Gly Arg Phe Thr Ile Ser Arg Asp Asn Ala Lys Arg Thr Leu Tyr
65                  70                  75                  80 ctg cag atg aac tca ctg att gca gag gac aca gca gtg tac tac tgt     288
Leu Gln Met Asn Ser Leu Ile Ala Glu Asp Thr Ala Val Tyr Tyr Cys
                85                  90                  95 gcc aag aca gga gga ggg cgc tac aac tat ggc atg gac tac tgg ggc     336
Ala Lys Thr Gly Gly Gly Arg Tyr Asn Tyr Gly Met Asp Tyr Trp Gly
            100                 105                 110 cac gga acg agc ctg ttt gtc tca tct gcg tcg acc aca gcc ccc tct     384
His Gly Thr Ser Leu Phe Val Ser Ser Ala Ser Thr Thr Ala Pro Ser
        115                 120                 125 gtg ttc ccc ctg gcc cct tcc tgt ggg tca acc tct ggc agc aca gtg     432
Val Phe Pro Leu Ala Pro Ser Cys Gly Ser Thr Ser Gly Ser Thr Val
    130                 135                 140 gcc ctg gcg tgt ctt gtg tct ggc tac ttc cct gaa cct gtg aca gtc     480
Ala Leu Ala Cys Leu Val Ser Gly Tyr Phe Pro Glu Pro Val Thr Val
145                 150                 155                 160 agc tgg aac agc gga agc ctg acc tct gga gtg cac acc ttc ccc agt     528
Ser Trp Asn Ser Gly Ser Leu Thr Ser Gly Val His Thr Phe Pro Ser
                165                 170                 175 gtc ctg caa agc tca ggc ctg cac agc ctg tca agt atg gtg aca gtg     576
Val Leu Gln Ser Ser Gly Leu His Ser Leu Ser Ser Met Val Thr Val
            180                 185                 190 ccc agt agc agg tgg cct tct gaa acc ttt acc tgc aac gtg gtg cac     624
Pro Ser Ser Arg Trp Pro Ser Glu Thr Phe Thr Cys Asn Val Val His
        195                 200                 205 cct gca tcc aac acc aaa gtg gat aag cct gtt ttc aat gag tgc aga     672
Pro Ala Ser Asn Thr Lys Val Asp Lys Pro Val Phe Asn Glu Cys Arg
    210                 215                 220 tgc aca gat aca cct ccc tgc cct gtg cct gag cct ctg gga gga cca     720
Cys Thr Asp Thr Pro Pro Cys Pro Val Pro Glu Pro Leu Gly Gly Pro
225                 230                 235                 240 tca gtc ctg atc ttc cct cca aag cct aag gat atc ctg cgg atc acc     768
Ser Val Leu Ile Phe Pro Pro Lys Pro Lys Asp Ile Leu Arg Ile Thr
```

```
                     245                 250                 255
aga acc ccc gag gtc acc tgt gtc gtc ctg gat ctg ggc cgg gaa gat    816
Arg Thr Pro Glu Val Thr Cys Val Val Leu Asp Leu Gly Arg Glu Asp
            260                 265                 270 cct gaa gtg cag att agc tgg ttt gtg gac ggc aag gaa gtg cac aca    864
Pro Glu Val Gln Ile Ser Trp Phe Val Asp Gly Lys Glu Val His Thr
        275                 280                 285 gct aag acc caa tcc cgg gag cag cag ttc aat ggc acc tac cgg gtg    912
Ala Lys Thr Gln Ser Arg Glu Gln Gln Phe Asn Gly Thr Tyr Arg Val
    290                 295                 300 gtc tct gtc ctg ccc atc gag cac caa gat tgg ctg aca ggc aaa gag    960
Val Ser Val Leu Pro Ile Glu His Gln Asp Trp Leu Thr Gly Lys Glu
305                 310                 315                 320 ttt aag tgc cga gtc aac cac ata gat ctt ccc tcc cct att gag cgg    1008
Phe Lys Cys Arg Val Asn His Ile Asp Leu Pro Ser Pro Ile Glu Arg
                325                 330                 335 acc atc tcc aag gca cgg ggg cga gcg cac aaa ccc tct gtc tat gtg    1056
Thr Ile Ser Lys Ala Arg Gly Arg Ala His Lys Pro Ser Val Tyr Val
            340                 345                 350 ctg cct ccc tct ccc aaa gaa ttg agc tct agc gat aca gtg tca atc    1104
Leu Pro Pro Ser Pro Lys Glu Leu Ser Ser Ser Asp Thr Val Ser Ile
        355                 360                 365 acc tgc ctg atc aag gac ttc tac ccc cct gac att gat gtt gaa tgg    1152
Thr Cys Leu Ile Lys Asp Phe Tyr Pro Pro Asp Ile Asp Val Glu Trp
    370                 375                 380 caa tca aat ggg cag caa gaa cca gag aga aaa cac aga atg acc cct    1200
Gln Ser Asn Gly Gln Gln Glu Pro Glu Arg Lys His Arg Met Thr Pro
385                 390                 395                 400 cca cag ctg gat gag gac ggg tcc tac ttt ctg tac tct aaa ctt tcc    1248
Pro Gln Leu Asp Glu Asp Gly Ser Tyr Phe Leu Tyr Ser Lys Leu Ser
                405                 410                 415 gtg gac aag agc aga tgg cag cag gga gac cct ttc acc tgt gcg gtc    1296
Val Asp Lys Ser Arg Trp Gln Gln Gly Asp Pro Phe Thr Cys Ala Val
            420                 425                 430 atg cac gag aca ctg caa aac cac tac aca gat ctg tcc ttg agc cac    1344
Met His Glu Thr Leu Gln Asn His Tyr Thr Asp Leu Ser Leu Ser His
        435                 440                 445 tca cct ggc aag                                                    1356
Ser Pro Gly Lys
    450

<210> SEQ ID NO 28
<211> LENGTH: 452
<212> TYPE: PRT
<213> ORGANISM: Artificial Sequence
<220> FEATURE:
<223> OTHER INFORMATION: Synthetic Construct

<400> SEQUENCE: 28

Glu Val Gln Leu Val Glu Ser Gly Gly Asp Leu Val Lys Pro Ala Gly
1               5                   10                  15

Ser Leu Arg Leu Ser Cys Val Ala Ser Gly Tyr Pro Phe Thr Asn Tyr
            20                  25                  30

Gly Met Asn Trp Val Arg Gln Ala Pro Gly Lys Gly Leu Gln Trp Val
        35                  40                  45

Ala Trp Ile Asn Thr Tyr Thr Gly Glu Pro Ala Cys Ala Asp Asp Phe
    50                  55                  60

Arg Gly Arg Phe Thr Ile Ser Arg Asp Asn Ala Lys Arg Thr Leu Tyr
65                  70                  75                  80
```

```
Leu Gln Met Asn Ser Leu Ile Ala Glu Asp Thr Ala Val Tyr Tyr Cys
                 85                  90                  95

Ala Lys Thr Gly Gly Gly Arg Tyr Asn Tyr Gly Met Asp Tyr Trp Gly
            100                 105                 110

His Gly Thr Ser Leu Phe Val Ser Ser Ala Ser Thr Thr Ala Pro Ser
            115                 120                 125

Val Phe Pro Leu Ala Pro Ser Cys Gly Ser Thr Ser Gly Ser Thr Val
        130                 135                 140

Ala Leu Ala Cys Leu Val Ser Gly Tyr Phe Pro Glu Pro Val Thr Val
145                 150                 155                 160

Ser Trp Asn Ser Gly Ser Leu Thr Ser Gly Val His Thr Phe Pro Ser
                165                 170                 175

Val Leu Gln Ser Ser Gly Leu His Ser Leu Ser Ser Met Val Thr Val
            180                 185                 190

Pro Ser Ser Arg Trp Pro Ser Glu Thr Phe Thr Cys Asn Val Val His
        195                 200                 205

Pro Ala Ser Asn Thr Lys Val Asp Lys Pro Val Phe Asn Glu Cys Arg
210                 215                 220

Cys Thr Asp Thr Pro Pro Cys Pro Val Pro Glu Pro Leu Gly Gly Pro
225                 230                 235                 240

Ser Val Leu Ile Phe Pro Pro Lys Pro Lys Asp Ile Leu Arg Ile Thr
                245                 250                 255

Arg Thr Pro Glu Val Thr Cys Val Val Leu Asp Leu Gly Arg Glu Asp
            260                 265                 270

Pro Glu Val Gln Ile Ser Trp Phe Val Asp Gly Lys Glu Val His Thr
        275                 280                 285

Ala Lys Thr Gln Ser Arg Glu Gln Gln Phe Asn Gly Thr Tyr Arg Val
290                 295                 300

Val Ser Val Leu Pro Ile Glu His Gln Asp Trp Leu Thr Gly Lys Glu
305                 310                 315                 320

Phe Lys Cys Arg Val Asn His Ile Asp Leu Pro Ser Pro Ile Glu Arg
                325                 330                 335

Thr Ile Ser Lys Ala Arg Gly Arg Ala His Lys Pro Ser Val Tyr Val
            340                 345                 350

Leu Pro Pro Ser Pro Lys Glu Leu Ser Ser Ser Asp Thr Val Ser Ile
        355                 360                 365

Thr Cys Leu Ile Lys Asp Phe Tyr Pro Pro Asp Ile Asp Val Glu Trp
370                 375                 380

Gln Ser Asn Gly Gln Gln Glu Pro Glu Arg Lys His Arg Met Thr Pro
385                 390                 395                 400

Pro Gln Leu Asp Glu Asp Gly Ser Tyr Phe Leu Tyr Ser Lys Leu Ser
                405                 410                 415

Val Asp Lys Ser Arg Trp Gln Gln Gly Asp Pro Phe Thr Cys Ala Val
            420                 425                 430

Met His Glu Thr Leu Gln Asn His Tyr Thr Asp Leu Ser Leu Ser His
        435                 440                 445

Ser Pro Gly Lys
    450

<210> SEQ ID NO 29
<211> LENGTH: 636
<212> TYPE: DNA
<213> ORGANISM: Artificial Sequence
<220> FEATURE:
<223> OTHER INFORMATION: Full Length antibody light chain coding with
```

```
                         canine CDR sequence
<220> FEATURE:
<221> NAME/KEY: CDS
<222> LOCATION: (1)..(636)

<400> SEQUENCE: 29 gat ata gtg atg acc caa acc cct cta agc cta tct gtc tcc cct ggg      48
Asp Ile Val Met Thr Gln Thr Pro Leu Ser Leu Ser Val Ser Pro Gly
 1               5                  10                  15 gag ccg gcg agt atc agc tgc agc gcc acc agc agc gtg tca tat atc      96
Glu Pro Ala Ser Ile Ser Cys Ser Ala Thr Ser Ser Val Ser Tyr Ile
             20                  25                  30 cac tgg tac ctg caa aag gct gga cag tcc cct aga ctt ctg ccc gaa     144
His Trp Tyr Leu Gln Lys Ala Gly Gln Ser Pro Arg Leu Leu Pro Glu
         35                  40                  45 agc aca tct aac ctg gcc agc ggg gtc cct gtg agg ttt agt ggg agt     192
Ser Thr Ser Asn Leu Ala Ser Gly Val Pro Val Arg Phe Ser Gly Ser
     50                  55                  60 ggg agt ggc acc gat ttc acc ctc cga att gga agg gtg gag gcc gaa     240
Gly Ser Gly Thr Asp Phe Thr Leu Arg Ile Gly Arg Val Glu Ala Glu
 65                  70                  75                  80 gat gct gga atc tat tac tgt cag caa aga agc agc tac ccc cct acc     288
Asp Ala Gly Ile Tyr Tyr Cys Gln Gln Arg Ser Ser Tyr Pro Pro Thr
                 85                  90                  95 ttc ggg cag ggc acc aga ctt gag gtc cgc agg aat gat gct cag cct     336
Phe Gly Gln Gly Thr Arg Leu Glu Val Arg Arg Asn Asp Ala Gln Pro
            100                 105                 110 gct gtg tac ctt ttt caa cca agc cct gac caa ctg cat acc ggc agt     384
Ala Val Tyr Leu Phe Gln Pro Ser Pro Asp Gln Leu His Thr Gly Ser
        115                 120                 125 gcc tct gtg gtc tgc ctg ctt aat agc ttc tat ccc aag gac att aat     432
Ala Ser Val Val Cys Leu Leu Asn Ser Phe Tyr Pro Lys Asp Ile Asn
    130                 135                 140 gtg aag tgg aag gtt gac ggc gtg ata cag gat acc gga att cag gaa     480
Val Lys Trp Lys Val Asp Gly Val Ile Gln Asp Thr Gly Ile Gln Glu
145                 150                 155                 160 agt gtg aca gaa caa gat aag gat agc acc tat agc ctg tct agc acc     528
Ser Val Thr Glu Gln Asp Lys Asp Ser Thr Tyr Ser Leu Ser Ser Thr
                165                 170                 175 ctc acc atg agc agc aca gag tac ttg agt cat gag ctg tat agc tgt     576
Leu Thr Met Ser Ser Thr Glu Tyr Leu Ser His Glu Leu Tyr Ser Cys
            180                 185                 190 gag att acc cac aag agt ctg cca agc acc ctt ata aaa agt ttc cag     624
Glu Ile Thr His Lys Ser Leu Pro Ser Thr Leu Ile Lys Ser Phe Gln
        195                 200                 205 cga tct gag tgt                                                     636
Arg Ser Glu Cys
    210

<210> SEQ ID NO 30
<211> LENGTH: 212
<212> TYPE: PRT
<213> ORGANISM: Artificial Sequence
<220> FEATURE:
<223> OTHER INFORMATION: Synthetic Construct

<400> SEQUENCE: 30

Asp Ile Val Met Thr Gln Thr Pro Leu Ser Leu Ser Val Ser Pro Gly
 1               5                  10                  15

Glu Pro Ala Ser Ile Ser Cys Ser Ala Thr Ser Ser Val Ser Tyr Ile
             20                  25                  30
```

```
His Trp Tyr Leu Gln Lys Ala Gly Gln Ser Pro Arg Leu Pro Glu
         35                  40                  45

Ser Thr Ser Asn Leu Ala Ser Gly Val Pro Val Arg Phe Ser Gly Ser
 50                  55                  60

Gly Ser Gly Thr Asp Phe Thr Leu Arg Ile Gly Arg Val Glu Ala Glu
 65                  70                  75                  80

Asp Ala Gly Ile Tyr Tyr Cys Gln Gln Arg Ser Ser Tyr Pro Pro Thr
                 85                  90                  95

Phe Gly Gln Gly Thr Arg Leu Glu Val Arg Arg Asn Asp Ala Gln Pro
                100                 105                 110

Ala Val Tyr Leu Phe Gln Pro Ser Pro Asp Gln Leu His Thr Gly Ser
            115                 120                 125

Ala Ser Val Val Cys Leu Leu Asn Ser Phe Tyr Pro Lys Asp Ile Asn
        130                 135                 140

Val Lys Trp Lys Val Asp Gly Val Ile Gln Asp Thr Gly Ile Gln Glu
145                 150                 155                 160

Ser Val Thr Glu Gln Asp Lys Asp Ser Thr Tyr Ser Leu Ser Ser Thr
                165                 170                 175

Leu Thr Met Ser Ser Thr Glu Tyr Leu Ser His Glu Leu Tyr Ser Cys
            180                 185                 190

Glu Ile Thr His Lys Ser Leu Pro Ser Thr Leu Ile Lys Ser Phe Gln
        195                 200                 205

Arg Ser Glu Cys
    210
```

<210> SEQ ID NO 31
<211> LENGTH: 1368
<212> TYPE: DNA
<213> ORGANISM: Artificial Sequence
<220> FEATURE:
<223> OTHER INFORMATION: Full length antibody heavy chain with feline CDR
<220> FEATURE:
<221> NAME/KEY: CDS
<222> LOCATION: (1)..(1368)

<400> SEQUENCE: 31

```
gac gtg cag ctg atg gag tct ggg ggc gac cta gtc aag cct ggg ggg    48
Asp Val Gln Leu Met Glu Ser Gly Gly Asp Leu Val Lys Pro Gly Gly
 1               5                  10                  15 tcc ctg cgg ctt acg tgt gtg gca agt ggg tac ccc ttc acc aac tat    96
Ser Leu Arg Leu Thr Cys Val Ala Ser Gly Tyr Pro Phe Thr Asn Tyr
                20                  25                  30 gga atg aac tgg gtc aga cag gcc cct gga aaa ggc ctg cag tgg gtg   144
Gly Met Asn Trp Val Arg Gln Ala Pro Gly Lys Gly Leu Gln Trp Val
            35                  40                  45 gcc tgg atc aac acc tat aca gga gaa cct gcc tgt gca gat gac ttt   192
Ala Trp Ile Asn Thr Tyr Thr Gly Glu Pro Ala Cys Ala Asp Asp Phe
 50                  55                  60 aga ggc cga ttc acc att tca aga gat aac gcg aag cga acc ttg tac   240
Arg Gly Arg Phe Thr Ile Ser Arg Asp Asn Ala Lys Arg Thr Leu Tyr
 65                  70                  75                  80 tta cag atg aac tcc ctg atc aca gaa gac aca gca acc tac tac tgt   288
Leu Gln Met Asn Ser Leu Ile Thr Glu Asp Thr Ala Thr Tyr Tyr Cys
                85                  90                  95 acc cgg aca gga ggg ggc cgc tac aac tat ggc atg gac tac tgg ggg   336
Thr Arg Thr Gly Gly Gly Arg Tyr Asn Tyr Gly Met Asp Tyr Trp Gly
                100                 105                 110 caa gga gca ctg gtg aca gtc tca tct gcg tcg acc aca gcc ccc tct   384
```

```
                Gln Gly Ala Leu Val Thr Val Ser Ser Ala Ser Thr Thr Ala Pro Ser
                                115                 120                 125 gtg ttc ccc ctg gcc cct tct tgt gga acc acc tct gga gcg aca gtg             432
Val Phe Pro Leu Ala Pro Ser Cys Gly Thr Thr Ser Gly Ala Thr Val
        130                 135                 140 gct ctg gcg tgc ctt gtc ctg ggg tac ttc cct gaa cct gtg acc gtc             480
Ala Leu Ala Cys Leu Val Leu Gly Tyr Phe Pro Glu Pro Val Thr Val
145                 150                 155                 160 agc tgg aac tcc gga gca ctg aca tct gga gtg cac acc ttt cct gcg             528
Ser Trp Asn Ser Gly Ala Leu Thr Ser Gly Val His Thr Phe Pro Ala
                165                 170                 175 gtc ctg caa gct tcc ggc ctg tac tca ctg tcc agc atg gtg act gtg             576
Val Leu Gln Ala Ser Gly Leu Tyr Ser Leu Ser Ser Met Val Thr Val
        180                 185                 190 cct tct tca aga tgg ctg tct gac acg ttc acc tgc aat gtg gcg cac             624
Pro Ser Ser Arg Trp Leu Ser Asp Thr Phe Thr Cys Asn Val Ala His
                195                 200                 205 cct cct tca aac aca aag gtc gat aag acc gtg aga aag aca gac cac             672
Pro Pro Ser Asn Thr Lys Val Asp Lys Thr Val Arg Lys Thr Asp His
210                 215                 220 ccc cct ggc cca aag ccc tgc gac tgt cct aag tgc ccc cct cct gaa             720
Pro Pro Gly Pro Lys Pro Cys Asp Cys Pro Lys Cys Pro Pro Pro Glu
225                 230                 235                 240 atg ctg ggc ggc ccc agc atc ttc ata ttc ccc cct aag ccc aaa gac             768
Met Leu Gly Gly Pro Ser Ile Phe Ile Phe Pro Pro Lys Pro Lys Asp
                245                 250                 255 acc ttg agt atc tct cga aca cca gaa gtc acc tgc ctg gtg gtg gac             816
Thr Leu Ser Ile Ser Arg Thr Pro Glu Val Thr Cys Leu Val Val Asp
                260                 265                 270 cta ggc cct gat gac tct gat gtg caa ata acc tgg ttc gtg gac aac             864
Leu Gly Pro Asp Asp Ser Asp Val Gln Ile Thr Trp Phe Val Asp Asn
        275                 280                 285 acc cag gtg tac acc gcc aaa acc tcc cca aga gag gag cag ttc aac             912
Thr Gln Val Tyr Thr Ala Lys Thr Ser Pro Arg Glu Glu Gln Phe Asn
290                 295                 300 tcc acc tat cgg gtc gtt agt gtg ctg ccc att ctg cac caa gac tgg             960
Ser Thr Tyr Arg Val Val Ser Val Leu Pro Ile Leu His Gln Asp Trp
305                 310                 315                 320 ctg aaa ggc aag gag ttc aag tgc aag gtc aat agc aaa tca ctg ccc            1008
Leu Lys Gly Lys Glu Phe Lys Cys Lys Val Asn Ser Lys Ser Leu Pro
                325                 330                 335 tct ccc att gaa aga acc att agc aag gcc aag gga cag ccc cac gaa            1056
Ser Pro Ile Glu Arg Thr Ile Ser Lys Ala Lys Gly Gln Pro His Glu
                340                 345                 350 cct cag gtg tat gtg ctg cca cct gcc cag gaa gag ctc agc cgc aac            1104
Pro Gln Val Tyr Val Leu Pro Pro Ala Gln Glu Glu Leu Ser Arg Asn
        355                 360                 365 aag gtc tct gtg acc tgc ctg atc aag tcc ttc cac cct cct gac ata            1152
Lys Val Ser Val Thr Cys Leu Ile Lys Ser Phe His Pro Pro Asp Ile
370                 375                 380 gca gtg gag tgg gaa ata aca gga cag cct gag cct gaa aac aac tac            1200
Ala Val Glu Trp Glu Ile Thr Gly Gln Pro Glu Pro Glu Asn Asn Tyr
385                 390                 395                 400 cgc acc acc cct ccc caa ctg gac tcc gat gga acc tac ttt gtc tac            1248
Arg Thr Thr Pro Pro Gln Leu Asp Ser Asp Gly Thr Tyr Phe Val Tyr
                405                 410                 415 tct aag ctg tct gtg gat cga agc cac tgg caa agg ggc aac acc tac            1296
Ser Lys Leu Ser Val Asp Arg Ser His Trp Gln Arg Gly Asn Thr Tyr
        420                 425                 430
```

```
acc tgc tct gtc agc cac gaa gcc ctg cac agc cac cac acc caa aag    1344
Thr Cys Ser Val Ser His Glu Ala Leu His Ser His His Thr Gln Lys
        435                 440                 445 tcc ctg acc cag agc ccc gga aag                                    1368
Ser Leu Thr Gln Ser Pro Gly Lys
450                 455

<210> SEQ ID NO 32
<211> LENGTH: 456
<212> TYPE: PRT
<213> ORGANISM: Artificial Sequence
<220> FEATURE:
<223> OTHER INFORMATION: Synthetic Construct

<400> SEQUENCE: 32

Asp Val Gln Leu Met Glu Ser Gly Gly Asp Leu Val Lys Pro Gly Gly
1               5                   10                  15

Ser Leu Arg Leu Thr Cys Val Ala Ser Gly Tyr Pro Phe Thr Asn Tyr
            20                  25                  30

Gly Met Asn Trp Val Arg Gln Ala Pro Gly Lys Gly Leu Gln Trp Val
        35                  40                  45

Ala Trp Ile Asn Thr Tyr Thr Gly Glu Pro Ala Cys Ala Asp Asp Phe
    50                  55                  60

Arg Gly Arg Phe Thr Ile Ser Arg Asp Asn Ala Lys Arg Thr Leu Tyr
65                  70                  75                  80

Leu Gln Met Asn Ser Leu Ile Thr Glu Asp Thr Ala Thr Tyr Tyr Cys
                85                  90                  95

Thr Arg Thr Gly Gly Gly Arg Tyr Asn Tyr Gly Met Asp Tyr Trp Gly
            100                 105                 110

Gln Gly Ala Leu Val Thr Val Ser Ser Ala Ser Thr Thr Ala Pro Ser
        115                 120                 125

Val Phe Pro Leu Ala Pro Ser Cys Gly Thr Thr Ser Gly Ala Thr Val
    130                 135                 140

Ala Leu Ala Cys Leu Val Leu Gly Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ala Ser Gly Leu Tyr Ser Leu Ser Ser Met Val Thr Val
            180                 185                 190

Pro Ser Ser Arg Trp Leu Ser Asp Thr Phe Thr Cys Asn Val Ala His
        195                 200                 205

Pro Pro Ser Asn Thr Lys Val Asp Lys Thr Val Arg Lys Thr Asp His
    210                 215                 220

Pro Pro Gly Pro Lys Pro Cys Asp Cys Pro Lys Cys Pro Pro Pro Glu
225                 230                 235                 240

Met Leu Gly Gly Pro Ser Ile Phe Ile Phe Pro Pro Lys Pro Lys Asp
                245                 250                 255

Thr Leu Ser Ile Ser Arg Thr Pro Glu Val Thr Cys Leu Val Val Asp
            260                 265                 270

Leu Gly Pro Asp Asp Ser Asp Val Gln Ile Thr Trp Phe Val Asp Asn
        275                 280                 285

Thr Gln Val Tyr Thr Ala Lys Thr Ser Pro Arg Glu Glu Gln Phe Asn
    290                 295                 300

Ser Thr Tyr Arg Val Val Ser Val Leu Pro Ile Leu His Gln Asp Trp
305                 310                 315                 320

Leu Lys Gly Lys Glu Phe Lys Cys Lys Val Asn Ser Lys Ser Leu Pro
```

```
                  325                 330                 335
Ser Pro Ile Glu Arg Thr Ile Ser Lys Ala Lys Gly Gln Pro His Glu
              340                 345                 350

Pro Gln Val Tyr Val Leu Pro Pro Ala Gln Glu Glu Leu Ser Arg Asn
          355                 360                 365

Lys Val Ser Val Thr Cys Leu Ile Lys Ser Phe His Pro Pro Asp Ile
      370                 375                 380

Ala Val Glu Trp Glu Ile Thr Gly Gln Pro Glu Pro Glu Asn Asn Tyr
385                 390                 395                 400

Arg Thr Thr Pro Pro Gln Leu Asp Ser Asp Gly Thr Tyr Phe Val Tyr
                  405                 410                 415

Ser Lys Leu Ser Val Asp Arg Ser His Trp Gln Arg Gly Asn Thr Tyr
              420                 425                 430

Thr Cys Ser Val Ser His Glu Ala Leu His Ser His His Thr Gln Lys
          435                 440                 445

Ser Leu Thr Gln Ser Pro Gly Lys
      450                 455

<210> SEQ ID NO 33
<211> LENGTH: 648
<212> TYPE: DNA
<213> ORGANISM: Artificial sequence
<220> FEATURE:
<223> OTHER INFORMATION: Full-length antibody light chain with feline
      CDR
<220> FEATURE:
<221> NAME/KEY: CDS
<222> LOCATION: (1)..(648)

<400> SEQUENCE: 33 gac atc gtg atg acc caa acc cct ctg agc ctg tcc gtc acc ccc ggg       48
Asp Ile Val Met Thr Gln Thr Pro Leu Ser Leu Ser Val Thr Pro Gly
1               5                   10                  15 gag ccc gcc agc ata agc tgc tcc gct acc agc tcc gtt agc tac att       96
Glu Pro Ala Ser Ile Ser Cys Ser Ala Thr Ser Ser Val Ser Tyr Ile
            20                  25                  30 cac tgg tat ctg caa aag cct ggc cag agc cct agg cga ctg atc tat      144
His Trp Tyr Leu Gln Lys Pro Gly Gln Ser Pro Arg Arg Leu Ile Tyr
        35                  40                  45 agc acc tcc aac ctg gcc tct ggt gtg cca gtg cgc ttc tct ggg tct      192
Ser Thr Ser Asn Leu Ala Ser Gly Val Pro Val Arg Phe Ser Gly Ser
    50                  55                  60 ggc agc ggg acc gac ttt acc ctg agg atc tcc aga gtg gag gct gat      240
Gly Ser Gly Thr Asp Phe Thr Leu Arg Ile Ser Arg Val Glu Ala Asp
65                  70                  75                  80 gat gtg ggg gtg tac tac tgc cag cag agg agc agc tat cct cct acc      288
Asp Val Gly Val Tyr Tyr Cys Gln Gln Arg Ser Ser Tyr Pro Pro Thr
                85                  90                  95 ttt ggc ccc ggc acc aag ctg gag ata aag agg agt gat gcc cag ccc      336
Phe Gly Pro Gly Thr Lys Leu Glu Ile Lys Arg Ser Asp Ala Gln Pro
            100                 105                 110 agc gtg ttt ctg ttc caa cct tct ctg gat gag ctg cac acc ggg agc      384
Ser Val Phe Leu Phe Gln Pro Ser Leu Asp Glu Leu His Thr Gly Ser
        115                 120                 125 gcc tct ata gtg tgt att ctg aat gat ttc tat ccc aaa gaa gtt aat      432
Ala Ser Ile Val Cys Ile Leu Asn Asp Phe Tyr Pro Lys Glu Val Asn
    130                 135                 140 gtc aag tgg aag gtg gat ggg gtg gtc cag aac aag ggc atc cag gaa      480
Val Lys Trp Lys Val Asp Gly Val Val Gln Asn Lys Gly Ile Gln Glu
145                 150                 155                 160
```

-continued

```
agc acg acc gaa cag aac tcc aag gac tcc aca tat tct ctg agt agt       528
Ser Thr Thr Glu Gln Asn Ser Lys Asp Ser Thr Tyr Ser Leu Ser Ser
            165                 170                 175 acc ctg acc atg agt agc acc gaa tac cag agt cac gag aaa ttc agc       576
Thr Leu Thr Met Ser Ser Thr Glu Tyr Gln Ser His Glu Lys Phe Ser
            180                 185                 190 tgc gag gtg acc cac aag agc ttg gcc agc acc cta gtg aag agc ttt       624
Cys Glu Val Thr His Lys Ser Leu Ala Ser Thr Leu Val Lys Ser Phe
            195                 200                 205 aac cga agc gag tgc cag cga gaa                                       648
Asn Arg Ser Glu Cys Gln Arg Glu
            210                 215

<210> SEQ ID NO 34
<211> LENGTH: 216
<212> TYPE: PRT
<213> ORGANISM: Artificial sequence
<220> FEATURE:
<223> OTHER INFORMATION: Synthetic Construct

<400> SEQUENCE: 34

Asp Ile Val Met Thr Gln Thr Pro Leu Ser Leu Ser Val Thr Pro Gly
1               5                   10                  15

Glu Pro Ala Ser Ile Ser Cys Ser Ala Thr Ser Ser Val Ser Tyr Ile
            20                  25                  30

His Trp Tyr Leu Gln Lys Pro Gly Gln Ser Pro Arg Arg Leu Ile Tyr
        35                  40                  45

Ser Thr Ser Asn Leu Ala Ser Gly Val Pro Val Arg Phe Ser Gly Ser
    50                  55                  60

Gly Ser Gly Thr Asp Phe Thr Leu Arg Ile Ser Arg Val Glu Ala Asp
65                  70                  75                  80

Asp Val Gly Val Tyr Tyr Cys Gln Gln Arg Ser Ser Tyr Pro Pro Thr
                85                  90                  95

Phe Gly Pro Gly Thr Lys Leu Glu Ile Lys Arg Ser Asp Ala Gln Pro
            100                 105                 110

Ser Val Phe Leu Phe Gln Pro Ser Leu Asp Glu Leu His Thr Gly Ser
        115                 120                 125

Ala Ser Ile Val Cys Ile Leu Asn Asp Phe Tyr Pro Lys Glu Val Asn
    130                 135                 140

Val Lys Trp Lys Val Asp Gly Val Val Gln Asn Lys Gly Ile Gln Glu
145                 150                 155                 160

Ser Thr Thr Glu Gln Asn Ser Lys Asp Ser Thr Tyr Ser Leu Ser Ser
                165                 170                 175

Thr Leu Thr Met Ser Ser Thr Glu Tyr Gln Ser His Glu Lys Phe Ser
            180                 185                 190

Cys Glu Val Thr His Lys Ser Leu Ala Ser Thr Leu Val Lys Ser Phe
        195                 200                 205

Asn Arg Ser Glu Cys Gln Arg Glu
    210                 215
```

VETERINARY COMPOSITION AND METHODS FOR NON-SURGICAL NEUTERING AND CASTRATION

CROSS-REFERENCE TO RELATED APPLICATIONS

This application is a 371 of PCT/US2013/062078, filed Sep. 27, 2013, which claims the benefit of the priority of U.S. Provisional Patent Application No. 61/785,547, filed Mar. 14, 2013, now expired, and U.S. Provisional Patent Application No. 61/707,900, filed Sep. 29, 2012, now expired. These priority applications are hereby incorporated by reference herein.

BACKGROUND OF THE INVENTION

Gonadotropin Releasing Hormone ("GnRH", also known as Luteinizing Hormone Releasing Hormone, or "LHRH"), is of importance to the regulation of fertility. Johnson M., Everitt B. *Essential Reproduction,* 3rd Edn. Blackwell Scientific Publications, 1988. The gonadotropin hormonal cascade can be halted by neutralization of the biological activity of GnRH. Fraser H. M. Physiological Effects of Antibody to Leutenizing Hormone Releasing Hormone.
In: *Physiological Effects of Immunity Against Reproductive Hormones*, Edwards and Johnson, Eds. Cambridge University Press, 1976. The use of antibodies to neutralize GnRH has been described as an effective means of contraception. See, U.S. Pat. No. 6,303,123. The scientific and patent literature has described inducing these antibodies by active immunization with GnRH immunogens or by passive immunization by administering anti-GnRH antibodies. Fraser H. M. Physiological Effects of Antibody to Leutenizing Hormone Releasing Hormone.
In: *Physiological Effects of Immunity Against Reproductive Hormones*, Edwards and Johnson, Eds. Cambridge University Press, 1976. Since anti-GnRH antibodies can neutralize the biological activity of GnRH, immunization constitutes an important approach towards treating diseases dependent upon gonadal steroids and other reproductive hormones as well as a means to regulate mammalian fertility.

GnRH has the same amino acid sequence in all mammals (pGlu-His-Trp-Ser-Tyr-Gly-Leu-Arg-Pro-GlyNH$_2$) (SEQ ID NO: 1); thus, it has been reported that a single immunogen would be effective in all mammalian species, including humans. However, attempts to induce antibodies or deliver anti-GnRH have been ineffective or have required repeated administration, which is impractical.

There is a good deal of literature describing the ability of antibodies targeting GnRH to safely and effectively inhibit reproductive function in many mammalian species, including rodents [Proc. Natl. Acad. Sci. (1985) 82, 1228-1231], cats [*Journal of Reproductive Immunology* (2004) 64, 107-119] and dogs [PNAS, cited above; Vaccine (2007) 25, 7111-7119]. Attempts to translate this observation into a useful means of nonsurgical sterilization, however, have been hampered by limitations in the currently available strategies for eliciting an effective antibody response to GnRH. GnRH vaccines have been developed using a wide array of adjuvants and carrier proteins, and some of these have even seen limited use in livestock and domestic animals [Clin. Microbiol. Rev. (2007) 20, 489-510]. Despite the promise of this approach, widespread utilization has been prevented by inconsistency in the induction and maintenance of the humoral immune response to GnRH, even after multiple immunizations Alternatively, passive immunization via direct administration of a neutralizing monoclonal antibody to GnRH has been shown to reliably suppress GnRH activity, but has not represented a practical option for sterilization given the need for repeated antibody administration.

What is needed is a practical, non-surgical veterinary method for neutering and castration of non-human animals.

SUMMARY OF THE INVENTION

In one embodiment, the invention provides a veterinary method for the nonsurgical sterilization of non-human mammals which involves AAV-mediated delivery of anti-GnRH neutralizing antibodies or proteins.

In one aspect, the invention provides a composition comprising an adeno-associated virus (AAV) vector having an AAV capsid having packaged therein nucleic acid sequences comprising an AAV 5' inverted terminal repeat (ITR), a sequence encoding a polypeptide which specifically binds gonadotropin releasing hormone (GnRH) under control of regulatory sequences which direct expression of an anti-GnRH polypeptide, and an AAV 3' ITR. The polypeptide may be an anti-GnRH antibody, immunoadhesin, a functional portion of the antibody which neutralizes GnRH, or a fusion protein comprising a functional portion of the antibody which neutralizes GnRH. The composition may contain about $10^9$ to about $5 \times 10^{13}$ vector particles per 1 mL aqueous suspension.

In one embodiment, the composition is adapted for delivery to domesticated pets, including dogs and cats. In another embodiment, the composition is adapted for delivery to horses, cows, pigs, sheep, or goats. In a further embodiment, the composition is formulated for intramuscular delivery. In a further embodiment, the composition is formulation for intravenous delivery.

In a further aspect, the invention provides an AAV encoding an IgG immunoglobulin having complementarity determining regions from an anti-GnRH immunoglobulin of a first animal species and framework regions from a second animal species. In one example, the polypeptide is an IgG1 antibody.

In still another embodiment, the invention provides a purified rAAV encoding an anti-GnRH antibody polypeptide. The anti-GnRH polypeptide coding sequences may be optimized for canine or feline delivery.

In yet another embodiment, the invention provides a lyophilized composition comprising the AAV-anti-GnRH polypeptide. In a further embodiment, the invention provides a reconstituted composition comprising the lyophilized composition and about $10^9$ to about $5 \times 10^{13}$ vector particles per 1 mL aqueous suspension.

In another aspect, the invention provides a method for non-surgical neutering or castration of a non-human mammal which comprises delivering to a non-human mammal an effective amount of the composition or purified rAAV described herein. The method may involve expressing the anti-GnRH polypeptide under the control of a constitutive promoter or a regulatable promoter. Optionally, the regulatable promoter is induced by a small molecule drug.

In still another aspect, the invention provides a method for inhibiting tumor growth in a human or non-human mammal with a hormone responsive cancer comprising delivering an amount of the composition or purified rAAV as described herein. The cancer may be breast or prostate cancer. In one embodiment, the delivery is via intravenous delivery.

In another embodiment, the invention provides a novel anti-GnRH polypeptide construct. In one embodiment, the construct is labeled for use in diagnosis or monitoring therapy. In another embodiment, the novel anti-GnRH polypeptide construct is admixed with a pharmaceutically acceptable carrier for delivery in a therapeutic regimen, e.g., an anti-neoplastic regimen. The anti-GnRH polypeptide construct may be species adapted for humans.

In a further embodiment, the invention provides a method for improving the taste of meat derived from a male pig, said method comprising the step of delivering a composition as described herein to the pig in order to reduce hormone levels following maturation of the male pig.

Still other aspects and embodiments of the invention will be apparent from the following detailed description of the invention.

Figure 1:
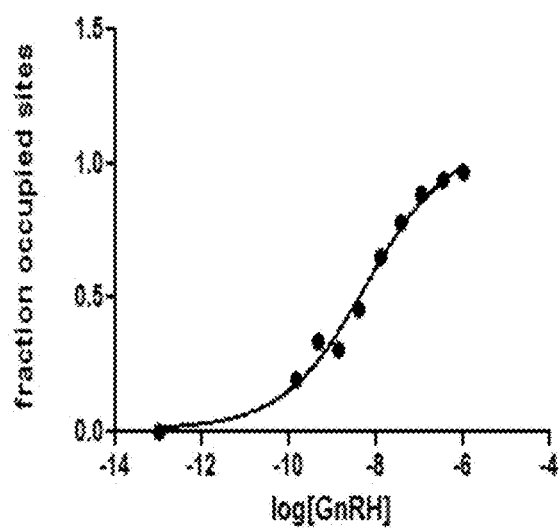
FIG. 1 is a graph showing the fraction of occupied antigen binding sites for the chimeric GnRH antibody incubated with different concentrations of GnRH. Competition ELISA and calculations were performed as previously described (Friguet et al., *J Immunol Methods*. 1985; 77(2): 305-319 and Stevens F. *Mol Immunol*. 1987; 24 (10): 1055-1060). Each point is calculated from the mean absorbance value of three wells.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987), Chothia, or AbM. There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. CDRs provide the majority of contact residues for the binding of the antibody to the antigen or epitope. CDRs of interest in this invention are derived from an anti-GnRH donor antibody variable heavy and light chain sequences, and include analogs of the naturally occurring CDRs, which analogs also share or retain the anti-GnRH antigen binding specificity and/or neutralizing ability as the donor antibody from which they were derived.

A "functional fragment" is a partial heavy or light chain variable sequence (e.g., minor deletions at the amino or carboxy terminus of the immunoglobulin variable region) which retains the same antigen binding specificity and/or neutralizing ability as the antibody from which the fragment was derived.

The terms Fv, Fc, Fd, Fab, or F(ab)2 are used with their standard meanings (see, e.g., Harlow et al., Antibodies A Laboratory Manual, Cold Spring Harbor Laboratory, (1988)).

As used herein, an immunoadhesin is an antibody-like molecule that fuses the Fc region of an immunoglobulin and the ligand-binding region of a receptor or adhesion molecule.

As used herein, an "engineered antibody" describes a type of altered antibody, i.e., a full-length synthetic antibody (e.g., a chimeric, reshaped or species adapted antibody as opposed to an antibody fragment) in which a portion of the light and/or heavy chain variable domains of a selected acceptor antibody are replaced by analogous parts from one or more donor antibodies which have specificity for the GnRH and in the instance of a bifunctional antibody, a second selected epitope. For example, such molecules may include antibodies characterized by a species adapted heavy chain associated with an unmodified light chain (or chimeric light chain), or vice versa. Engineered antibodies may also be characterized by alteration of the nucleic acid sequences encoding the acceptor antibody light and/or heavy variable domain framework regions in order to retain donor antibody binding specificity. These antibodies can comprise replacement of one, two, three, four, five or all six CDRs from the acceptor antibody with CDRs from a donor antibody described herein.

A "chimeric antibody" refers to a type of engineered antibody which contains a naturally-occurring variable region (light chain and heavy chains) derived from a donor antibody in association with light and heavy chain constant regions derived from an acceptor antibody.

An "analog" is an amino acid sequence modified by at least one amino acid, wherein said modification can be chemical or a substitution or a rearrangement of a few amino acids (i.e., no more than 10), which modification permits the amino acid sequence to retain the biological characteristics, e.g., antigen specificity and high affinity, of the unmodified sequence. For example, (silent) mutations can be constructed, via substitutions, when certain endonuclease restriction sites are created within or surrounding CDR-encoding regions. The present invention contemplates the use of analogs of the antibody of the invention. It is well known that minor changes in amino acid or nucleic acid sequences may lead, e.g., to an allelic form of the original protein which retains substantially similar properties. Thus analogs of the antibody of the invention includes those in which the CDRs in the hypervariable region of the heavy and light chains are at least 80% homologous, preferably at least 90% homologous and more preferably at least 95% homologous to the CDRs as defined above as CDRH1, CDRH2, CDRH3, CDRL1, CDRL2 and CDRL3 and retain GnRH neutralizing activity Amino acid sequences are at least 80% homologous if they have 80% identical amino acid residues in a like position when the sequences are aligned optimally, gaps or insertions being counted as non-identical residues. The invention also contemplates analogs of the antibodies of the invention wherein the framework regions are at least 80%, preferably at least 90% and more preferably at least 95% homologous to the framework regions set forth herein Amino acid sequences are at least 80% homologous if they have 80% identical amino acid residues in a like position when the sequences are aligned optimally, gaps or insertions being counted as non-identical residues.

Identity or similarity with respect to a sequence is defined herein as the percentage of amino acid residues in the candidate sequence that are identical (i.e., same residue) or similar (i.e., amino acid residue from the same group based on common side-chain properties, see below) with the peptide and polypeptide regions of the anti-GnRH antibodies provided herein, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

Percent (%) identity is a measure of the relationship between two polynucleotides or two polypeptides, as determined by comparing their nucleotide or amino acid sequences, respectively. In general, the two sequences to be compared are aligned to give a maximum correlation between the sequences. The alignment of the two sequences is examined and the number of positions giving an exact amino acid or nucleotide correspondence between the two sequences determined, divided by the total length of the alignment and multiplied by 100 to give a % identity figure. This % identity figure may be determined over the whole length of the sequences to be compared, which is particularly suitable for sequences of the same or very similar length and which are highly homologous, or over shorter defined lengths, which is more suitable for sequences of unequal length or which have a lower level of homology. There are a number of algorithms, and computer programs based thereon, which are available to be used the literature and/or publically or commercially available for performing alignments and percent identity. The selection of the algorithm or program is not a limitation of the present invention.

Examples of suitable alignment programs including, e.g., the software CLUSTALW under Unix and then be imported into the Bioedit program (Hall, T. A. 1999, BioEdit: a user-friendly biological sequence alignment editor and analysis program for Windows 95/98/NT. Nucl. Acids. Symp. Ser. 41:95-98); the Wisconsin Sequence Analysis Package, version 9.1 (Devereux J. et al., Nucleic Acids Res., 12:387-395, 1984, available from Genetics Computer Group, Madison, Wis., USA). The programs BESTFIT and GAP, may be used to determine the % identity between two polynucleotides and the % identity between two polypeptide sequences. Other programs for determining identity and/or similarity between sequences include, e.g., the BLAST family of programs available from the National Center for Biotechnology Information (NCB), Bethesda, Md., USA and accessible through the home page of the NCBI at www.ncbi.nlm.nih.gov), the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used; and FASTA (Pearson W. R. and Lipman D. J., Proc. Natl. Acad. Sci. USA, 85:2444-2448, 1988, available as part of the Wisconsin Sequence Analysis Package). SeqWeb Software (a web-based interface to the GCG Wisconsin Package: Gap program).

Analogs may also arise as allelic variations. An "allelic variation or modification" is an alteration in the nucleic acid sequence. Such variations or modifications may be due to degeneracy in the genetic code or may be deliberately engineered to provide desired characteristics. These variations or modifications may or may not result in alterations in any encoded amino acid sequence.

As used throughout this specification and the claims, the terms "comprising" and "including" are inclusive of other components, elements, integers, steps and the like. Conversely, the term "consisting" and its variants are exclusive of other components, elements, integers, steps and the like. The term "about" encompasses a variation within and including ±10%, unless otherwise specified.

The polypeptide delivered via an AAV vector may be selected from an anti-GnRH antibody, immunoadhesin, a functional portion of the antibody which neutralizes GnRH, or an immunoglobulin fusion protein comprising a functional portion of the antibody which neutralizes GnRH. The functional portion of the antibody which neutralizes GnRH may be selected from a Fab, Fab', scFv, or a heavy chain variable domain. For convenience throughout the remainder of this specification, the term "anti-GnRH polypeptide" is used to encompass each of the types of constructs described in this paragraph and specification.

Anti-GnRH Polypeptide

The term "species-adapted" anti-GnRH polypeptide refers to anti-GnRH polypeptide containing at least CDRs from a donor antibody grafted or fused onto constant regions of an acceptor immunoglobulin of an isotype and subclass which is compatible with the species to which the anti-GnRH polypeptide is to be delivered. "Species-adapted" may include humanized antibodies, unless veterinary or non-human donors or targets are specified. "Veterinary species-adapted" excludes humanized antibodies.

In one embodiment, the invention provides a recombinant AAV having packaged therein an anti-GnRH polypeptide. In order to construct this species-adapted anti-GnRH polypeptide, the complementarity determining regions (CDRs) from any of a number of donor monoclonal antibodies which specifically bind and neutralize GnRH can be utilized. In one embodiment, the monoclonal antibody is derived from a single species. For example, an antibody can be induced in a selected animal, e.g., by injection of a GnRH or GnRH-derived polypeptide, and used in the present invention to construct an anti-GnRH polypeptide. Injection may be performed using methods described in the literature in order to induce self-antibodies to GnRH. See, e.g., "Active Immunization against gonadotropin-releasing hormone: an effective tool to block the fertility axis in mammals", Jouwert Anne Turkstra—[S.1.]:[s.n.], 2005—Tekst.—Proefschrift Universiteit Utrecht, http://igitur-archive.library.uu.nl/dissertations/2006-0117-200157/c5.pdf. B. Fromme, et al, "A Novel Retro-Inverso Gonadotropin-Releasing Hormone (GnRH) Immunogen Elicits Antibodies That Neutralize the Activity of Native GnRH", Endocrinology (Jul. 1, 2003) vol. 144 no. 7 3262-3269 (Published online before print Apr. 3, 2003). A neutralizing antibody may be generated using the GnRH isoform which is common to all mammals (GnRH-I), or another species GnRH isoform, such as is provided in the table below.

| Amino acid sequences of GnRH isoforms | |
|---|---|
| Mammalian GnRH (GnRH I) | SEQ ID NO: 1: pEHWSYGLRPG# |
| Chicken GnRH II (GnRH II) | SEQ ID NO: 2: pEHWSHGWYPG# |
| Salmon GnRH (salmon GnRH I) | SEQ ID NO: 3: pEHWSYGWLPG# |
| Lamprey GnRH I (lamprey GnRH I) | SEQ ID NO: 4: pEHYSLEWKPG# |
| Lamprey GnRH III (lamprey GnRH III) | SEQ ID NO: 5: pEHWSHDWKPG# | pE = pyroglutamic acid;
# = amide;
Underlined amino acid differ from GnRH-I amino acid sequence.

GnRH has the same amino acid sequence in all mammals (pGlu-His-Trp-Ser-Tyr-Gly-Leu-Arg-Pro-GlyNH$_2$) (SEQ ID NO: 1). Alternatively, an anti-GnRH monoclonal antibody from a mouse, rat, rabbit or species other source can be serve as a donor antibody to generate an engineered antibody for AAV-mediated delivery to a heterologous species. Such an anti-GnRH monoclonal antibody may be obtained from amongst those previously described, e.g., a murine IgG1 monoclonal antibody produced by hybridoma USASK/DSIL-LHRH-A1, and available from the ATCC under Accession Number HB-9094, 10801 University Blvd. Manassas, Va. 20110-2209 USA (Silversides D W, et al. J. Reprod. Immunol. 7: 171-184, 1985, characterized by the authors as having a specificity by showing 1%, 0.03% and 0.0001% binding of salmon GnRH, D-Leu6-GnRH and TRH, respectively. Urbanski, H F. Biology of Reproduction 44: 681-686, 1991, which describe HU4H and HU11B; both of which belong to the IgG1 subclass; Carson et al., Theriogenology 48: 193-207, 1997, describing three murine monoclonals of IgG2a class immunoglobulins which bound 50% I-125-GnRH at a $10^6$ to $10^7$ dilution, were specific to GnRH, showed a strong affinity ($K_a$ values from 1.99 to $2.60 \times 10^{10}$ liters/mole), and were directed towards the amino terminus; and Talwar, G P et al. Proc. Natl. Acad. Sci. USA 82: 1228-1231, 1985, describes a hybridoma P$_8$16$_{62}$ producing a MAb of IgG2a class with a κ light chain, and having a $K_a$ of $1.2 \times 10^9$ liter/ml as determined by Scatchard plot.

Alternatively, other anti-GnRH antibodies may be generated using techniques known to those of skill in the art. [Riechmann L, Clark M, Waldmann H, Winter G (March 1988). "Reshaping human antibodies for therapy". Nature 332 (6162): 323-327, which includes a description of "humanizing" antibodies; Köhler, G.; Milstein, C. (1975). "Continuous cultures of fused cells secreting antibody of predefined specificity". Nature 256 (5517): 495-497; Schmitz U, Versmold A, Kaufmann P, Frank H G (2000). "Phage display: a molecular tool for the generation of antibodies—a review". Placenta 21 (Suppl A): S106-S112, describes production of recombinant antibodies, all incorporated herein by reference].

In one embodiment, the donor amino acid sequences are derived from the HB-9094 murine antibody variable light, variable heavy, or CDR sequence.

VL Amino Acid Sequence, using single letter codes: SEQ ID NO: 6

QIVLTQSPAIMSASPGEKVTITCSATSSVSYIHWFQQKPGTSPKLWIYST

SNLASGVP(V)RFSGSGSGTSYSLTISRMEAEDAATYYCQQRSSYPPTFG

GGTKLEIKR or an amino acid sequence having about 97% to about 99% identity therewith.

In one embodiment, the coding sequence of this VL region is: SEQ ID NO: 7

CAAATTGTTCTCACCCAGTCTCCAGCCATCATGTCTGCATCTCCAGGGGA

GAAGGTCACCATAACCTGCAGTGCCACTCAAGTGTAAGTTACATACACTG

GTTCCAGCAGAAGCCAGGCACTTCTCCCAAACTCTGGATTTATAGCACAT

CCAACCTGGCTTCTGGAGTCCCTGTTCGCTTCAGTGGCAGTGGATCTGGG

ACCTCTTACTCTCTCACAATCAGCCGAATGGAGGCTGAAGATGCTGCCAC

TTATTACTGCCAGCAAAGGAGTAGTTACCCACCCACGTTCGGAGGGGGA

CCAACTGGAAATAAAACGVHCAGATCCAGTTGGTGCAGTCTGGACCTGAA

CTGAAGAAGCCTGGAGAGACAGTCAAGATCTCCTGCAAGGCTTCTGGATA

TCCCTTCACAAACTATGGAATGAACTGGGTGAAGCAGGCTCCAGGAAAGG

GTTTAAAGTGGATGGGCTGGATAAACACCTACACTGGAGAGCCAGCATGT

GCTGATGACTTCAGGGGACGGTTTGCCATCTCTTTGGAAACCTCCGCCAG

ACTGCCTATTTGCAGATCAACAACCTCATAAATGAGGACACGGCAACATA

TTTCTGTGCAAGAACGGGGGGTGGTAGGTACAACTATGGTATGGACTATT

GGGGTCAAGGAACCTCAGTCACCGTCTCCTCA,
or a sequence about 97% to about 99% identical therewith.

In another embodiment, the donor amino acid sequences are from a canine variable light:
SEQ ID NO: 8:

DIVMTQTPLSLSVSPGEPASISCSATSSVSYIHWYLQKAGQSPRLLPEST

SNLASGVPVRFSGSGSGTDFTLRIGRVEAEDAGIYYCQQRSSYPPTFGQG

TRLEVRR,
or asequence about 97% to about 99% identical therewith.

SEQ ID NO: 9:

GATATAGTGATGACCCAAACCCCTCTAAGCCTATCTGTCTCCCCTGGGGA

GCCGGCGAGTATCAGCTGCAGCGCCACCAGCAGCGTGTCATATATCCACT

GGTACCTGCAAAAGGCTGGACAGTCCCCTAGACTTCTGCCCGAAAGCACA

TCTAACCTGGCCAGCGGGGTCCCTGTGAGGTTTAGTGGGAGTGGGAGTGG

CACCGATTTCACCCTCCGAATTGGAAGGGTGGAGGCCGAAGATGCTGGAA

TCTATTACTGTCAGCAAAGAAGCAGCTACCCCCCTACCTTCGGGCAGGGC

ACCAGACTTGAGGTCCGCAGGAATGATGCTCAGCCTGCTGTGTACCTTTT

TCAACCAAGCCCTGACCAACTGCATACCGGCAGTGCCTCTGTGGTCTGCC

TGCTTAATAGCTTCTATCCCAAGGACATTAATGTGAAGTGGAAGGTTGAC

GGCGTGATACAGGATACCGGAATTCAGGAAAGTGTGACAGAACAAGATAA

GGATAGCACCTATAGCCTGTCTAGCACCCTCACCATGAGCAGCACAGAGT

ACTTGAGTCATGAGCTGTATAGCTGTGAGATTACCCACAAGAGTCTGCCA

AGCACCCTTATAAAAAGTTTCCAGCGATCTGAGTGT,
or a sequence about 97% to about 99%
identical therewith.

In another embodiment, the donor amino acid sequences are from a feline variable light:
SEQ ID NO: 10:

DIVMTQTPLSLSVTPGEPASISCSATSSVSYIHWYLQKPGQSPRRLIYST

SNLASGVPVRFSGSGSGTDFTLRISRVEADDVGVYYCQQRSSYPPTFGPG

TKLEIKR,
or asequence about 97% to about
99% identical therewith.

In one embodiment, the coding sequence for the feline variable light is:
SEQ ID NO: 11:

GACATCGTGATGACCCAAACCCCTCTGAGCCTGTCCGTCACCCCCGGGGA

GCCCGCCAGCATAAGCTGCTCCGCTACCAGCTCCGTTAGCTACATTCACT

GGTATCTGCAAAAGCCTGGCCAGAGCCCTAGGCGACTGATCTATAGCACC

TCCAACCTGGCCTCTGGTGTGCCAGTGCGCTTCTCTGGGTCTGGCAGCGG

GACCGACTTTACCCTGAGGATCTCCAGAGTGGAGGCTGATGATGTGGGGG

TGTACTACTGCCAGCAGAGGAGCAGCTATCCTCCTACCTTTGGCCCCGGC

ACCAAGCTGGAGATAAAGAGGAGTGATGCCCAGCCCAGCGTGTTTCTGTT

CCAACCTTCTCTGGATGAGCTGCACACCGGGAGCGCCTCTATAGTGTGTA

TTCTGAATGATTTCTATCCCAAAGAAGTTAATGTCAAGTGGAAGGTGGAT

GGGGTGGTCCAGAACAAGGGCATCCAGGAAAGCACGACCGAACAGAACTC

CAAGGACTCCACATATTCTCTGAGTAGTACCCTGACCATGAGTAGCACCG

AATACCAGAGTCACGAGAAATTCAGCTGCGAGGTGACCCACAAGAGCTTG

GCCAGCACCCTAGTGAAGAGCTTTAACCGAAGCGAGTGCCAGCGAGAA,
or a sequence about 97% to about
99% identical therewith.

Alternatively, the coding sequences sequence may be optimized as described herein using degenerative codons, i.e., changing the codon without affecting the amino acid sequence. Such coding sequences have an identity as low as about 85% identity, or lower, with the coding sequence without changing the amino acid sequence. Alternatively, other modifications may be introduced.

In one embodiment the VH Amino Acid Sequence, using single letter codes is:
(a) a murine VH, SEQ ID NO: 12:

```
QIQLVQSGPELKKPGETVKISCKASGYPFTNYGMNWVKQAPGKGLKWMGW
INTYTGEPACADDFRGRFA(I)SLETSA(R)TAYLQINNL(I)NEDTATY
FCARTGGGRYNYGMDYWGQGTSVTVSS,
or sequence about 97% to about 99%
identical thereto.
```

In one embodiment, the coding sequence of this VH region is:
SEQ ID NO: 13:

```
CAGATCCAGTTGGTGCAGTCTGGACCTGAACTGAAGAAGCCTGGAGAGAC
AGTCAAGATCTCCTGCAAGGCTTCTGGATATCCCTTCACAAACTATGGAA
TGAACTGGGTGAAGCAGGCTCCAGGAAAGGGTTTAAAGTGGATGGGCTGG
ATAAACACCTACACTGGAGAGCCAGCATGTGCTGATGACTTCAGGGGACG
GTTTGCCATCTCTTTGGAAACCTCCGCCAGAACTGCCTATTTGCAGATCA
ACAACCTCATAAATGAGGACACGGCAACATATTTCTGTGCAAGAACGGGG
GGTGGTAGGTACAACTATGGTATGGACTATTGGGGTCAAGGAACCTCAGT
CACCGTCTCCTCA,
or a sequence about 97% to about 99% identical
thereto.
```

(b) a canine VH sequence: SEQ ID NO: 14:

```
EVQLVESGGDLVKPAGSLRLSCVASGYPFTNYGMNWVRQAPGKGLQWVAW
INTYTGEPACADDFRGRFTISRDNAKRTLYLQMNSLIAEDTAVYYCAKTG
GGRYNYGMDYWGHGTSLFVSS,
or a sequence about 97% to about 99%
identical thereto.
```

In one embodiment, the coding sequence of the canine VH region is
SEQ ID NO: 15:

```
gaggtgcagctggtggagagcggcggggatctggtcaagcctgccggcag
cctgagactgagctgcgtggcaagcggctaccccttcacaaattatggca
tgaactgggtgcgacaggcccctggcaagggcctgcagtgggtggcctgg
ataaacacctacaccggggaaccagcatgtgcagatgacttcagaggccg
cttcaccatatctcgagacaatgctaagcggaccctgtatctgcagatga
actcactgattgcagaggacacagcagtgtactactgtgccaagacagga
ggagggcgctacaactatggcatggactactggggccacggaacgagcct
gtttgtctcatctgcgtcgaccacagcccctctgtgttcccctggccc
cttcctgtgggtcaacctctggcagcacagtggccctggcgtgtcttgtg
tctggctacttccctgaacctgtgacagtcagctggaacagcggaagcct
gacctctggagtgcacaccttccccagtgtcctgcaaagctcaggcctgc
``` acagcctgtcaagtatggtgacagtgcccagtagcaggtggccttctgaa
acctttacctgcaacgtggtgcaccctgcatccaacaccaaagtggataa
gcctgttttcaatgagtgcagatgcacagatacacctccctgccctgtgc
ctgagcctctgggaggaccatcagtcctgatcttccctccaaagcctaag
gatatcctgcggatcaccagaaccccgaggtcacctgtgtcgtcctgga
tctgggccgggaagatcctgaagtgcagattagctggtttgtggacggca
aggaagtgcacacagctaagacccaatcccgggagcagcagttcaatggc
acctaccgggtggtctctgtcctgcccatcgagcaccaagattggctgac
aggcaaagagtttaagtgccgagtcaaccacatagatcttccctcccta
ttgagcggaccatctccaaggcacggggggcgagcgcacaaaccctctgtc
tatgtgctgcctccctctcccaaagaattgagctctagcgatacagtgtc
aatcacctgcctgatcaaggacttctaccccctgacattgatgttgaat
ggcaatcaaatgggcagcaagaaccagagagaaaacacagaatgacccct
ccacagctggatgaggacgggtcctactttctgtactctaaactttccgt
ggacaagagcagatggcagcagggagacccctttcacctgtgcggtcatgc
acgagacactgcaaaaccactacacagatctgtccttgagccactcacct
ggcaag,
or sequences about 97% to about 99%
identical thereto.

(c) a feline VH: SEQ ID NO: 16:

```
DVQLMESGGDLVKPGGSLRLTCVASGYPFTNYGMNWVRQAPGKGLQWVAW
INTYTGEPACADDFRGRFTISRDNAKRTLYLQMNSLITEDTATYYCTRTG
GGRYNYGMDYWGQGALVTVSS,
or a sequence about 97% to about 99%
identical thereto.
```

In one embodiment, the coding sequence for this feline VH is, SEQ ID NO: 17:

acgtgcagctgatggagtctgggggcgacctagtcaagcctgggggtcc
ctgcggcttacgtgtgtggcaagtgggtaccccttcaccaactatggaat
gaactgggtcagacaggcccctggaaaaggcctgcagtgggtggcctgga
tcaacacctatacaggagaacctgcctgtgcagatgactttagaggccga
ttcaccatttcaagagataacgcgaagcgaaccttgtacttacagatgaa
ctccctgatcacagaagacacagcaacctactactgtacccggacaggag
ggggccgctacaactatggcatggactactggggcaaggagcactggtg
acagtctcatctgcgtcgaccacagcccctctgtgttccccctggcccc
ttcttgtggaaccacctctggagcgacagtggctctggcgtgccttgtcc
tggggtacttccctgaacctgtgaccgtcagctggaactccggagcactg
acatctggagtgcacacctttcctgcggtcctgcaagcttccggcctgta
ctcactgtccagcatggtgactgtgccttcttcaagatggctgtctgaca
cgttcacctgcaatgtggcgcaccctcctttcaaacacaaaggtcgataag
accgtgagaaagacagaccaccccccctggcccaaagcccgcgactgtcc

```
taagtgccccctcctgaaatgctgggcggcccagcatcttcatattcc cccctaagcccaaagacaccttgagtatctctcgaacaccagaagtcacc tgcctggtggtggacctaggccctgatgactctgatgtgcaaataacctg gttcgtggacaacacccaggtgtacaccgccaaaacctccccaagagagg agcagttcaactccacctatcgggtcgttagtgtgctgcccattctgcac caagactggctgaaaggcaaggagttcaagtgcaaggtcaatagcaaatc actgccctctcccattgaaagaaccattagcaaggccaagggacagcccc acgaacctcaggtgtatgtgctgccacctgcccaggaagagctcagccgc aacaaggtctctgtgacctgcctgatcaagtccttccaccctcctgacat agcagtggagtgggaaataacaggacagcctgagcctgaaaacaactacc gcaccacccctcccaactggactccgatggaacctactttgtctactct aagctgtctgtggatcgaagccactggcaaaggggcaacacctacacctg ctctgtcagccacgaagccctgcacagccaccacacccaaaagtccctga cccagagccccggaaag,
or a sequence about 97% to about 99%
identical thereto.
```

In one embodiment, the donor amino acid sequences are of the antibody variable light, variable heavy, or CDR sequence.

In still another embodiment, allelic and other variants of this coding sequence or fragments of this coding sequence, e.g., such as those fragments encoding desired CDRs may be used. These variants may be naturally occurring or engineered. For example, the coding sequence may be optimized as described herein using degenerative codons, i.e., changing the codon without affecting the amino acid sequence. Alternatively, other modifications may be introduced.

Optionally, rather than using the entire VL or VH sequence, the sequences of the CDRs may be utilized to create an immunoglobulin construct. In such an instance, the somatic mutations, shown in the above sequence with ( ) may also be designed into the acceptor immunoglobulin sequences. Further, the immunoglobulin constructs described herein may also be engineered to contain leader sequences (i.e., translated regions 5' to the antibody coding region which direct intracellular trafficking, and which are removed prior to secretion) which are heterologous to the donor source or acceptor source, e.g., in order to permit or improve secretion of the antibody. For example, bacterial leader sequences may be selected (e.g., for in vitro expression of the antibody or other applications). Alternatively, mammalian leader sources for an immunoglobulin or from a non-immunoglobulin source may be selected. For example, one suitable leader sequence may be an IL-2 leader sequence. However, other suitable leader sequences are known to those of skill in the art.

An immunoglobulin construct of the invention may have a CDR VH1 with an amino acid sequence of GYPFT-NYGMN, SEQ ID NO: 18. Alternatively, an immunoglobulin construct of the invention may have CDR VH1 with an amino acid sequence GYPFTNY, SEQ ID NO: 19. In still another alternative, the amino acid sequence of the CDR VH1 is NYGMN, SEQ ID NO: 20. Additionally or alternatively, the amino acid sequence of the CDR VH2 is WIN-TYTGEPACADDFRGRF, SEQ ID NO: 21. Alternatively, the amino acid sequence of the CDR VH2 is WINTYT-GEPACA, SEQ ID NO: 22. Additionally or alternatively, the amino acid sequence of the CDR VH3 is TGGGRYNYG-MDY, SEQ ID NO: 23. Encompassed within the invention are sequences having about 97% to about 99% identity to one or more of the CDRs of VH1, VH2, and/or VH3.

An immunoglobulin construct of the invention may have a CDR VL1 amino acid sequence of SATSSVSYIH, SEQ ID NO: 24. Alternatively or additionally, an immunoglobulin construct of the invention may have a CDR VL2 may have an amino acid sequence of STSNLAS, SEQ ID NO: 25. Alternatively or additionally, an immunoglobulin construct of the invention may have a CDR VL3 has a sequence of QQRSSYPPT, SEQ ID NO: 26. Encompassed within the invention are sequences having about 97% to about 99% identity to one or more of the CDRs of VL1, VL2, and/or VL3.

In order to generate a species-adapted anti-GnRH polypeptide, the peptide sequence of one, two or preferably all three CDRs from each the light chain immunoglobulin and the heavy chain immunoglobulin, or both, from such an anti-GnRH monoclonal antibody are grafted onto or fused with the constant (framework) regions of an acceptor antibody. As used herein, once the sequences of the CDRs are identified, they may be produced synthetically, e.g., through chemical synthesis, or they may be obtained from the donor antibody using methods known in the art. An antibody subclass is determined by the constant region of the antibody. Preferably, the constant region of an engineered immunoglobulin or antibody is selected from an isotype and subclass which is naturally found in the species to which the AAV expressing the antibody is to be delivered. Optionally, the acceptor immunoglobulin is from the same species as the species to which the AAV is targeted. For example, a canine immunoglobulin framework would provide the constant regions of an engineered antibody construct to be delivered to dogs; a feline immunoglobulin would provide the constant regions of an engineered antibody construct to be delivered to cats; an equine immunoglobulin provides the constant regions of an engineered antibody construct to be delivered to horses; a bovine immunoglobulin provides the constant regions of an engineered antibody construct to be delivered to cows or bulls; a porcine immunoglobulin provides the constant regions of an engineered antibody construct to be delivered to pigs (pigs, hogs, swine) including sows and boars; a caprine immunoglobulin provides the constant regions of an engineered antibody construct to be delivered to goats. Still other mammalian immunoglobulins can be selected as needed or desired. For example, human immunoglobulin sources may be selected. Generally, the constant regions of an IgG are selected to provide desirable pharmacokinetic properties in vivo; however, another immunoglobulin type can be selected. The sequences of a variety of human and non-human mammalian, and other animal immunoglobulin sequences, are available from IMGT (THE INTERNATIONAL IMMUNOGENETICS INFORMATION SYSTEM®) http://www.imgt.org/, SwissProt, GenBank, http://www.kazusa.or.jp/codon/), or other sources.

In addition to one or more of the CDRs from the donor antibody, additional sequences from the donor antibody may be included to form a species-adapted anti-GnRH polypeptide. These additional sequences may include additional sequences from the variable region of the donor antibody. Additionally, somatic mutations may be incorporated as well. Optionally, one may also engineer out glycosylation signals, amino acid isomerization sites, and proteolytic sites. In another embodiment, mutations can be introduced into Fc chains for greater stability and half-life or better clearance.

Canine antibody heavy chain amino acid sequence, SEQ ID NO: 28:

EVQLVESGGDLVKPAGSLRLSCVASGYPFTNYGMNWVRQAPGKGLQWVAW
INTYTGEPACADDFRGRFTISRDNAKRTLYLQMNSLIAEDTAVYYCAKTG
GGRYNYGMDYWGHGTSLFVSSASTTAPSVFPLAPSCGSTSGSTVALACLV
SGYFPEPVTVSWNSGSLTSGVHTFPSVLQSSGLHSLSSMVTVPSSRWPSE
TFTCNVVHPASNTKVDKPVFNECRCTDTPPCPVPEPLGGPSVLIFPPKPK
DILRITRTPEVTCVVLDLGREDPEVQISWFVDGKEVHTAKTQSREQQFNG
TYRVVSVLPIEHQDWLTGKEFKCRVNHIDLPSPIERTISKARGRAHKPSV
YVLPPSPKELSSSDTVSITCLIKDFYPPDIDVEWQSNGQQEPERKHRMTP
PQLDEDGSYFLYSKLSVDKSRWQQGDPFTCAVMHETLQNHYTDLSLSHSP
GK

Feline antibody heavy chain amino acid sequence, SEQ ID NO: 32:

DVQLMESGGDLVKPGGSLRLTCVASGYPFTNYGMNWVRQAPGKGLQWVAW
INTYTGEPACADDFRGRFTISRDNAKRTLYLQMNSLITEDTATYYCTRTG
GGRYNYGMDYWGQGALVTVSSASTTAPSVFPLAPSCGTTSGATVALACLV
LGYFPEPVTVSWNSGALTSGVHTFPAVLQASGLYSLSSMVTVPSSRWLSD
TFTCNVAHPPSNTKVDKTVRKTDHPPGPKPCDCPKCPPPEMLGGPSIFIF
PPKPKDTLSISRTPEVTCLVVDLGPDDSDVQITWFVDNTQVYTAKTSPRE
EQFNSTYRVVSVLPILHQDWLKGKEFKCKVNSKSLPSPIERTISKAKGQP
HEPQVYVLPPAQEELSRNKVSVTCLIKSPHPPDIAVEWEITGQPEPENNY
RTTPPQLDSDGTYFVYSKLSVDRSHWQRGNTYTCSVSHEALHSHHTQKSL
TQSPGK

Canine antibody light chain amino acid sequence, SEQ ID NO: 30:

DIVMTQTPLSLSVSPGEPASISCSATSSVSYIHWYLQKAGQSPRLLPEST
SNLASGVPVRFSGSGSGTDFTLRIGRVEAEDAGIYYCQQRSSYPPTFGQG
TRLEVRRNDAQPAVYLFQPSPDQLHTGSASVVCLLNSFYPKDINVKWKVD
GVIQDTGIQESVTEQDKDSTYSLSSTLTMSSTEYLSHELYSCFITHKSLP
STLIKSFQRSEC

Feline antibody light chain amino acid sequence, SEQ ID NO: 34:

DIVMTQTPLSLSVTPGEPASISCSATSSVSYIHWYLQKPGQSPRRLIYST
SNLASGVPVRFSGSGSGTDFTLRISRVEADDVGVYYCQQRSSYPPTFGPG

TKLEIKRSDAQPSVFLFQPSLDELHTGSASIVCILNDFYPKEVNWKWKVD
GVVQNKGIQESTTEQNSKDSTYSLSSTLTMSSTEYQSHEKFSCEVTHKSL
ASTLVKSFNRSECQRE

Canine antibody heavy chain nucleotide sequence, SEQ ID NO: 27:

gaggtgcagaggtggagagcggcggggatctggtcaagcctgccggcagc
ctgagactgagagcgtggcaagcggctacccatcacaaattatggcatga
actgggtgcgacaggccctggcaagggcctgcagtgggtggcctggata
aacacctacaccggggaaccagcatgtgcagatgacttcagaggccgctt
caccatatacgagacaatgctaagcggaccagtatctgcagatgaactca
ctgattgcagaggacacagcagtgtactactgtgccaagacaggaggagg
gcgctacaactatggcatggactactggggccacggaacgagcctgtttg
tctcatctgcgtcgaccacagcccctagtgttccccctggcccatcctg
tgggtcaacctaggcagcacagtggccaggcgtgtcttgtgtaggctact
tccctgaacctgtgacagtcagaggaacagcggaagcctgacctaggagt
gcacaccttccccagtgtcctgcaaagctcaggcctgcacagcctgtcaa
gtatggtgacagtgcccagtagcaggtggccttctgaaacctttacctgc
aacgtggtgcaccagcatccaacaccaaagtggataagcctgttttcaat
gagtgcagatgcacagatacacctccctgccagtgcctgagcctagggag
gaccatcagtcctgatatccaccaaagcctaaggatatcctgcggatcac
cagaaccccgaggtcacctgtgtcgtcctggatctgggccgggaagatc
ctgaagtgcagattagctggtttgtggacggcaaggaagtgcacacagct
aagacccaatcccgggagcagcagttcaatggcacctaccgggtggtctc
tgtcctgcccatcgagcaccaagattggctgacaggcaaagagtttaagt
gccgagtcaaccacatagatcttccacccctattgagcggaccataccaa
ggcacgggggcgagcgcacaaaccactgtctatgtgctgcctccctaccc
aaagaattgagactagcgatacagtgtcaatcacctgcctgatcaaggac
ttctaccccagacattgatgttgaatggcaatcaaatgggcagcaagaa
ccagagagaaaacacagaatgacccctccacagctggatgaggacgggtc
ctactttctgtactctaaactttccgtggacaagagcagatggcagcagg
gagaccattcacctgtgcggtcatgcacgagacactgcaaaaccactaca
cagatctgtccttgagccactcacctggcaag Canine antibody light chain nucleotide sequence, SEQ ID NO: 29:

GATATAGTGATGACCCAAACCCCTCTAAGCCTATCTGTCTCCCCTGGGGA
GCCGGCGAGTATCAGCTGCAGCGCCACCAGCAGCGTGTCATATATCCACT
GGTACCTGCAAAAGGCTGGACAGTCCCCTAGACTTCTGCCCGAAAGCACA
TCTAACCTGGCCAGCGGGGTCCCTGTGAGGTTTAGTGGGAGTGGGAGTGG

-continued
CACCGATTTCACCCTCCGAATTGGAAGGGTGGAGGCCGAAGATGCTGGAA

TCTATTACTGTCAGCAAAGAAGCAGCTACCCCCCTACCTTCGGGCAGGGC

ACCAGACTTGAGGTCCGCAGGAATGATGCTCAGCCTGCTGTGTACCTTTT

TCAACCAAGCCCTGACCAACTGCATACCGGCAGTGCCTCTGTGGTCTGCC

TGCTTAATAGCTTCTATCCCAAGGACATTAATGTGAAGTGGAAGGTTGAC

GGCGTGATACAGGATACCGGAATTCAGGAAAGTGTGACAGAACAAGATAA

GGATAGCACCTATAGCCTGTCTAGCACCCTCACCATGAGCAGCACAGAGT

ACTTGAGTCATGAGCTGTATAGCTGTGAGATTACCCACAAGAGTCTGCCA

Feline antibody heavy chain nucleotide sequence, SEQ ID NO: 31:

gacgtgcagctgatggagtctgggggcgacctagtcaagcctgggggtc cctgcggcttacgtgtgtggcaagtgggtacccccttcaccaactatggaa tgaactgggtcagacaggccctggaaaaggcctgcagtgggtggcctgg atcaacacctatacaggagaacctgcctgtgcagatgactttagaggccg attcaccatttcaagagataacgcgaagcgaaccttgtacttacagatga actccctgatcacagaagacacagcaacctactactgtacccggacagga gggggccgctacaactatggcatggactactgggggcaaggagcactggt gacagtctcatctgcgtcgaccacagcccctctgtgttcccctggccc cttcttgtggaaccacctctggagcgacagtggctctggcgtgccttgtc ctggggtacttccctgaacctgtgaccgtcagctggaactccggagcact gacatctggagtgcacacctttcctgcggtcctgcaagcttccggcctgt actcactgtccagcatggtgactgtgccttcttcaagatggctgtctgac acgttcacctgcaatgtggcgcaccctccttcaaacacaaaggtcgataa gaccgtgagaaagacagaccacccccctggcccaaagccctgcgactgtc ctaagtgccccctcctgaaatgctgggcggcccccagcatcttcatattc cccctaagcccaaagaccttgagtatctctcgaacaccagaagtcac ctgcctggtggtggacctaggccctgatgactctgatgtgcaaataacct ggttcgtggacaacacccaggtgtacaccgccaaaacctccccaagagag gagcagttcaactccacctatcgggtcgttagtgtgctgcccattctgca ccaagactggctgaaaggcaaggagttcaagtgcaaggtcaatagcaaat cactgccctctcccattgaaagaaccattagcaaggccaagggacagccc cacgaacctcaggtgtatgtgctgccacctgcccaggaagagctcagccg caacaaggtctctgtgacctgcctgatcaagtccttccaccctcctgaca tagcagtggagtgggaaataacaggacagcctgagcctgaaaacaactac cgcaccacccctccccaactggactccgatggaacctactttgtctactc taagctgtctgtggatcgaagccactggcaaaggggcaacacctacacct gctctgtcagccacgaagccctgcacagccaccacacccaaaagtccctg acccagagccccggaaag Feline antibody light chain nucleotide sequence, SEQ ID NO: 33:

GACATCGTGATGACCCAAACCCCTCTGAGCCTGTCCGTCACCCCCGGGGA

GCCCGCCAGCATAAGCTGCTCCGCTACCAGCTCCGTTAGCTACATTCACT

GGTATCTGCAAAAGCCTGGCCAGAGCCCTAGGCGACTGATCTATAGCACC

TCCAACCTGGCCTCTGGTGTGCCAGTGCGCTTCTCTGGGTCTGGCAGCGG

GACCGACTTTACCCTGAGGATCTCCAGAGTGGAGGCTGATGATGTGGGGG

TGTACTACTGCCAGCAGAGGAGCAGCTATCCTCCTACCTTTGGCCCCGGC

ACCAAGCTGGAGATAAAGAGGAGTGATGCCCAGCCCAGCGTGTTTCTGTT

CCAACCTTCTCTGGATGAGCTGCACACCGGGAGCGCCTCTATAGTGTGTA

TTCTGAATGATTTCTATCCCAAAGAAGTTAATGTCAAGTGGAAGGTGGAT

GGGGTGGTCCAGAACAAGGGCATCCAGGAAAGCACGACCGAACAGAACTC

CAAGGACTCCACATATTCTCTGAGTAGTACCCTGACCATGAGTAGCACCG

AATACCAGAGTCACGAGAAATTCAGCTGCGAGGTGACCCACAAGAGCTTG

GCCAGCACCCTAGTGAAGAGCTTTAACCGAAGCGAGTGCCAGCGAGAA

An anti-GnRH polypeptide fusion protein is encompassed within the scope of the invention. For example, a functional portion of an antibody may be fused to a protein or peptide for a variety of reasons, e.g., to increase circulating half-life, to increase clearance, or to provide a desired biological function. For example, an immunoglobulin-cytokine fusion may be desired for use in a therapeutic regimen for cancers, particularly those associated with GnRH or hormones which are expressed downstream of GnRH. Such cancers may include breast cancer or prostate cancer. Examples of suitable cytokines which may form fusion partners with an immunoglobulin include, e.g., interleukin (IL)-2, IL-12, B7-1, and GM-CSF. In one embodiment, an AAV is engineered with an antibody fusion protein provides transport or improved through the blood brain barrier, e.g., to allow targeting of the pituitary. One example is to make a fusion protein with a naturally occurring peptides which improves transport across the blood-brain barrier, such as penetratin and SynB1 and Syn B3 (Rouselle et al (2000) Mol. Pharm. 57, 679-686 and Rouselle et al (2001) Journal of Pharmacology and Experimental Therapeutics 296, 124-131). Another example would be a bispecific antibody which in addition to targeting GnRH also is directed towards a brain capilliary endothelial cell receptor, e.g., an anti-insulin receptor antibody or anti-transferrin receptor antibody.

In one embodiment, these antibodies are expressed in vitro and utilized in protein form, e.g., for diagnostic purposes or in anti-neoplastic regimens, or for monitoring therapeutic expression levels in vitro. In such an instance, the antibody may be produced synthetically or recombinantly using any suitable in vitro expression system and from any suitable genetic element. For many of the applications described herein, however, the anti-GnRH polypeptides described herein are designed for delivery via an AAV particle.

In addition, the coding sequences for these anti-GnRH polypeptides or other proteins such as described herein may be optimized, e.g., for expression of the anti-GnRH polypeptide in the target species. For example, an AAV-anti-GnRH vector may be optimized for expression in a non-human mammal such as canines, felines, equine, bovine, ovine, caprine, porcine, and the like. Alternatively, the vector may be optimized for expression in a primate, including a human, e.g., for anti-neoplastic regimens or another desired therapy. Other optimization may involve selection of species-specific or tissue-specific promoters, linkers, IRES's and other elements which are found an AAV vector. Such vector elements are discussed in more detail below.

In addition to species-adapting an anti-GnRH polypeptide for a selected mammal species, the AAV capsid is also selected in order to preferentially target the animal species. The typical AAV capsid is composed of 60 copies of capsid protein subunits, VP1, VP2, and VP3, that are arranged in an icosahedral symmetry in a ratio of 1:1:10. It is the capsid which is responsible for tissue specificity. For example, AAV8 has been identified as being well suited for use in canines. Additionally, an AAV may be selected by taking into consideration the ability of a selected AAV to transduce and/or express in a selected target tissue. In one embodiment, the AAV is selected for targeting skeletal muscle. For example, AAV1, AAV6, AAV8, AAV9 have been described as being useful for transducing and expressing in muscle tissue. Further, the inventors have identified hu37, rh02, rh20, rh46, cy5, hu32, hu32/33 and pi2 as being useful in muscle transduction/expression. However, other AAV can be readily selected for another target tissue and/or for considerations relating to greater expression in a selected species. These and other sources of AAV and their capsids sequences have been described, e.g., WO 2003/042397A1 (May 22, 2003); WO 2005/033321 (Apr. 14, 2005); WO 2006/110689 (Oct. 19, 2006). Sequences of a variety of AAV are also available from GenBank.

Given this information, one can construct an AAV vector having the selected capsid and sequences encoding an anti-GnRH polypeptide using methods know to those of skill in the art. In one embodiment, an AAV vector contains sequences encoding only a single anti-GnRH polypeptide. However, an AAV vector may contain sequences encoding two or more anti-GnRH polypeptides. In still another embodiment, a mixture of two or more different AAV vectors containing different expression cassettes are co-administered. Such a mixture may contain AAV vectors with different subunits of a single anti-GnRH polypeptide. Alternatively, such a mixture may contain an AAV vector in which one subset of the vectors contains an expression cassette for an anti-GnRH polypeptide and a second subset of the vectors contains sequences for the control of expression of the first subset of vectors. The vectors and compositions described herein may be used in connection with the "Pharmacologically Induced Transgene Ablation System" described in PCT/US2011/030213, filed Mar. 28, 2011, published as WO 2011/126808, Oct. 13, 2011, or co-pending U.S. patent application Ser. No. 13/247,306, filed Sep. 28, 2011, both of which are incorporated by reference herein.

Production AAV Viral Particles

Methods of preparing AAV-based vectors are known. See, e.g., US Published Patent Application No. 2007/0036760 (Feb. 15, 2007), which is incorporated by reference herein. The sequences of any of the AAV capsids can be readily generated using a variety of techniques. Suitable production techniques are well known to those of skill in the art. See, e.g., Sambrook et al, Molecular Cloning: A Laboratory Manual, Cold Spring Harbor Press (Cold Spring Harbor, N.Y.). Alternatively, oligonucleotides encoding peptides (e.g., CDRs) or the peptides themselves can generated synthetically, e.g., by the well-known solid phase peptide synthesis methods (Merrifield, (1962) *J. Am. Chem. Soc.,* 85:2149; Stewart and Young, Solid Phase Peptide Synthesis (Freeman, San Francisco, 1969) pp. 27-62). These and other suitable production methods are within the knowledge of those of skill in the art and are not a limitation of the present invention.

Methods of generating a recombinant adeno-associated virus (AAV) such as are described herein are known. Such a method involves culturing a host cell which contains a nucleic acid sequence encoding an AAV capsid; a functional rep gene; a expression cassette composed of, at a minimum, AAV inverted terminal repeats (ITRs) and a transgene; and sufficient helper functions to permit packaging of the expression cassette into the AAV capsid protein.

The components required to be cultured in the host cell to package an AAV expression cassette in an AAV capsid may be provided to the host cell in trans. Alternatively, any one or more of the required components (e.g., expression cassette, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The expression cassette, rep sequences, cap sequences, and helper functions required for producing the rAAV of the invention may be delivered to the packaging host cell in the form of any genetic element which transfer the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, (1993) *J. Virol.,* 70:520-532 and U.S. Pat. No. 5,478,745.

Unless otherwise specified, the AAV ITRs, and other selected AAV components described herein, may be readily selected from among any AAV. These ITRs or other AAV components may be readily isolated using techniques available to those of skill in the art from an AAV sequence. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank®, PubMed®, or the like.

A. The Expression Cassette

The expression cassette is composed of, at a minimum, a transgene and its regulatory sequences, and 5' and 3' AAV inverted terminal repeats (ITRs). In one embodiment, the ITRs of AAV serotype 2 are used. However, ITRs from other suitable sources may be selected. It is this expression cassette that is packaged into a capsid protein and delivered to a selected host cell.

1. The Transgene

The transgene is a nucleic acid sequence, heterologous to the vector sequences flanking the transgene, which encodes anti-GnRH polypeptide or a subunit thereof, or another peptide, polypeptide, protein, or other product of interest. The nucleic acid coding sequence is operatively linked to regulatory components in a manner which permits transgene transcription, translation, and/or expression in a host cell.

The invention further includes using multiple transgenes. In certain situations, a different transgene may be used to encode each subunit of a protein, or to encode different peptides or proteins. This is desirable when the size of the DNA encoding the protein subunit is large, e.g., for an immunoglobulin. In order facilitate the cell to producing a multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M L Donnelly, et al, (January 1997) *J. Gen. Virol.*, 78(Pt 1):13-21; S. Furler, S et al, (June 2001) *Gene Ther.*, 8(11):864-873; H. Klump, et al., (May 2001) *Gene Ther.*, 8(10):811-817. This 2A peptide is significantly smaller than an IRES, making it well suited for use when space is a limiting factor. More often, when the transgene is large, consists of multi-subunits, or two transgenes are co-delivered, rAAV carrying the desired transgene(s) or subunits are co-administered to allow them to concatamerize in vivo to form a single vector genome. In such an embodiment, a first AAV may carry an expression cassette which expresses a single transgene and a second AAV may carry an expression cassette which expresses a different transgene for co-expression in the host cell. However, the selected transgene may encode any biologically active product or other product, e.g., a product desirable for study.

Suitable transgenes may be readily selected by one of skill in the art. The selection of the transgene is not considered to be a limitation of this invention.

2. Regulatory Elements

In addition to the major elements identified above for the expression cassette, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, (1985) *Cell*, 41:521-530], the SV40 promoter, the dihydrofolate reductase promoter, the β-actin promoter, the phosphoglycerol kinase (PGK) promoter, and the EF1 promoter [Invitrogen]. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system [International Patent Publication No. WO 98/10088]; the ecdysone insect promoter [No et al, (1996) *Proc. Natl. Acad. Sci. USA*, 93:3346-3351], the tetracycline-repressible system [Gossen et al, (1992) *Proc. Natl. Acad. Sci. USA*, 89:5547-5551], the tetracycline-inducible system [Gossen et al, (1995) *Science*, 268:1766-1769, see also Harvey et al, (1998) *Curr. Opin. Chem. Biol.*, 2:512-518], the RU486-inducible system [Wang et al, (1997) *Nat. Biotech.*, 15:239-243 and Wang et al, (1997) *Gene Ther.*, 4:432-441] and the rapamycin-inducible system [Magari et al, (1997) *J. Clin. Invest.*, 100:2865-2872], including, e.g., the Argent™ system which is available from Ariad. Other types of inducible promoters which may be useful in this context are those which are regulated by a specific physiological state, e.g., temperature, acute phase, a particular differentiation state of the cell, or in replicating cells only.

Another embodiment of the transgene includes a gene operably linked to a tissue-specific promoter. For instance, if expression in skeletal muscle is desired, a promoter active in muscle should be used. These include the promoters from genes encoding skeletal β-actin, myosin light chain 2A, dystrophin, desmin, MHC, muscle creatine kinase, as well as synthetic muscle promoters with activities higher than naturally-occurring promoters (see Li et al., (1999) *Nat. Biotech.*, 17:241-245). Examples of promoters that are tissue-specific are known for CNS/neuronal include, e.g., neuron-specific enolase (NSE) promoter (Andersen et al., (1993) *Cell. Mol. Neurobiol.*, 13:503-15), neurofilament light-chain gene (Piccioli et al., (1991) *Proc. Natl. Acad. Sci. USA*, 88:5611-5), and the neuron-specific vgf gene (Piccioli et al., (1995) *Neuron*, 15:373-84), among others. In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

The combination of the transgene, promoter/enhancer, and 5' and 3' AAV ITRs is referred to as an expression cassette for ease of reference herein. Provided with the teachings of this invention, the design of such an expression cassette can be made by resort to conventional techniques.

3. Delivery of the Expression Cassette to an AAV Packaging Host Cell

The expression cassette can be carried on any suitable vector, e.g., a plasmid, which is delivered to a host cell. The plasmids useful in this invention may be engineered such that they are suitable for replication and, optionally, integration in prokaryotic cells, mammalian cells, or both. These plasmids (or other vectors carrying the 5' AAV ITR-anti-GnRH-3' AAV ITR) contain sequences permitting replication of the expression cassette in eukaryotes and/or prokaryotes and selection markers for these systems. Selectable markers or reporter genes may include sequences encoding geneticin, hygromicin or purimycin resistance, among others. The plasmids may also contain certain selectable reporters or marker genes that can be used to signal the presence of the vector in bacterial cells, such as ampicillin resistance. Other components of the plasmid may include an origin of replication and an amplicon, such as the amplicon system employing the Epstein Barr virus nuclear antigen. This amplicon system, or other similar amplicon components permit high copy episomal replication in the cells. Preferably, the molecule carrying the expression cassette is transfected into the cell, where it may exist transiently. Alternatively, the expression cassette (carrying the 5' AAV ITR-anti-GnRH-3' ITR) may be stably integrated into the genome of the host cell, either chromosomally or as an episome. In certain embodiments, the expression cassette may be present in multiple copies, optionally in head-to-head, head-to-tail, or tail-to-tail concatamers. Suitable transfection techniques are known and may readily be utilized to deliver the expression cassette to the host cell.

Generally, when delivering the vector comprising the expression cassette by transfection, the vector is delivered in an amount from about 5 µg to about 100 µg DNA, about 10 µg to about 50 µg DNA to about $1 \times 10^4$ cells to about $1 \times 10^{13}$ cells, or about $1 \times 10^5$ cells. However, the relative amounts of vector DNA to host cells may be adjusted, taking into consideration such factors as the selected vector, the delivery method and the host cells selected.

B. Packaging Host Cells

In addition to the expression cassette, the host cell contains the sequences which drive expression of a AAV capsid protein of the invention in the host cell and rep sequences of the same source as the source of the AAV ITRs found in the expression cassette, or a cross-complementing source. The packaging host cell also requires helper functions in order to package the rAAV of the invention. Such helper functions are well known in the art and will not be duplicated herein. Similarly, methods for producing suitable vectors having AAV capsids are known. [See, e.g., US Published Patent Application No. US 2007/0036760].

The vectors and compositions described herein may be designed for use in the "Pharmacologically Induced Transgene Ablation System" described in PCT/US2011/030213, filed Mar. 28, 2011, published as WO 2011/126808, Oct. 13, 2011, or co-pending U.S. patent application Ser. No. 13/247,306, filed Sep. 28, 2011, both of which are incorporated by reference herein.

An anti-GnRH polypeptide construct of the invention may be delivered to host cells according to published methods. The construct of an rAAV encoding same can be suspended in a physiologically compatible carrier, may be administered to a veterinary or human subject. In one embodiment, the carrier is sterile saline alone or, optionally, with any of a number of buffering solutions (e.g., phosphate buffered saline). Other exemplary carriers include lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV (or the anti-GnRH polypeptide construct) and carrier(s), other conventional pharmaceutical ingredients, such as preservatives, or chemical stabilizers. The compositions are administered in sufficient amounts to transfect the cells and to provide sufficient levels of gene transfer and expression to neutralize GnRH. In one embodiment, delivery is via intramuscular or subcutaneous delivery. In another embodiment, delivery is via intravenous delivery. However, still other routes of administration may be selected. Alternatively or additionally, routes of administration may be combined, if desired.

In one embodiment, the invention includes a lyophilized composition which contains an rAAV as described herein, or a mixture of rAAV, in lyophilized form. Optionally, one or more stabilizers or preservatives is present in this composition. Suitably, for use, a lyophilized composition is reconstituted with a suitable diluent, e.g., sterile saline or a buffered saline.

Dosages of the viral vector will depend primarily on factors such as the condition being treated, the age, weight and health of the patient, and may thus vary among patients. For example, a therapeutically effective dosage of the viral vector is generally in the range of from about 0.1 mL to about 100 mL, or about 0.1 mL to about 10 mL, or about 0.1 mL to about 5 mL, or about 0.5 mL to about 1 mL, of solution containing concentrations of from about $1 \times 10^9$ to $1 \times 10^{16}$ genomes viral vector (particles)/mL aqueous suspending agent. One exemplary dosage is about $10^9$ to $5 \times 10^{13}$ AAV genomes/mL. Another exemplary dosage is about $5 \times 10^{10}$ to $5 \times 10^{13}$ AAV genomes per 1 kg. One suitable volume is about 1 mL. In another embodiment, a therapeutically effective dose of the anti-GnRH polypeptide construct is in the range of about 0.001 ng to about 1000 mg/70 kg animal, which may be delivered in a single dosage or over a series of two or more doses. Other suitable dosages may be determined The dosage will be adjusted to balance the therapeutic benefit against any side effects and such dosages may vary depending upon the therapeutic application for which the recombinant vector is employed.

Uses for Anti-GnRH Polypeptide Compositions

The AAV-mediated delivery of anti-GnRH polypeptides as described herein are useful for veterinary (non-human) non-surgical neutering or castration of a non-human mammal. In some embodiments, a series of two injections may be desired, e.g., at the same time or spaced apart. However, the method is suited to provide permanent neutering or castration following a single injection or of a composition containing the AAV.anti-GnRH polypeptide.

In other embodiments, a permanently reversible or a regulatable expression of the anti-GnRH polypeptide may be desired. This may be case in the instance of an animal for which it is desirable to prevent unwanted breeding, e.g., during show or racing season, to prevent ovulation including just prior to a breeding or fertilization attempt, or to otherwise control breeding. In such an instance, the anti-GnRH expression cassette may be designed to have a regulatable or inducible promoter and/or to be used in connection with the pharmacologically induced transgene ablation system discussed in the publications cited and incorporated by reference herein. Thus, the compositions of the invention may optionally be delivered in a regimen with another vector which contains further expression control sequences and/or a drug (e.g., a rapamycin or rapalog) which controls a regulatable promoter present in the AAV carrying the anti-GnRH polypeptide expression cassette or the ablation sequence. Such a regimen with an inducing agent may be used to induce expression of an inducible promoter throughout the time that fertility is being prevented. Alternatively, where transgene ablation is desired, the regimen may be started at a point when permanent ablation of anti-GnRH is desired, e.g., prevention of breeding is no longer desired.

In one embodiment, the target mammal is delivered an effective amount of a composition as described herein, which includes an rAAV or anti-GnRH polypeptide construct which is purified to meet regulatory requirements. The composition may be a reconstituted composition as described herein. Delivery may be via intramuscular, subcutaneous, or intravenous. However, other suitable routes of delivery may be selected.

It is anticipated that the non-surgical neutering and castration method of the invention will be particularly desired in domestic pets, including male and female dogs and cats. However, these methods will also be useful for non-domestic animals, including cows, bulls, sheep (ewes and rams), goats, pigs (sows and boar), horses (mares and stallions), deer, amongst others. In addition, the method of the invention is anticipated to be useful in reducing "meat taint", which is associated with the presence of sex hormones such as testosterone which are produced in mature animals, e.g., male pigs (boars) and goats. In this aspect of the invention, the composition of the invention may be delivered either prior to, or following maturation.

In still another embodiment, the invention provides a method for inhibiting tumor growth in a mammal with a hormone associated cancer (e.g., estrogen or testosterone). Such cancers may include, e.g, breast or prostate cancer and particularly hormone dependent breast or prostate cancer. In this aspect of the invention, a mammal (including, e.g., a human) may be treated in a regimen involving an AAV-anti-GnRH polypeptide as defined herein. When the polypeptide is delivered via AAV, the anti-GnRH polypeptide may be expressed under the control of an inducible or regulatable promoter so that the anti-GnRH polypeptide is only expressed in the presence of the inducing or regulating agent. Thus, the regimen may involve administration of an inducing or regulating agent such as are defined herein in order to expression the anti-GnRH polypeptide. The regimen may also involve one or more conventional chemotherapeutic agents. Typically, when used as an anti-neoplastic regimen as described herein, the anti-GnRH polypeptide delivery (including AAV-mediated delivery) is intravenous, although other suitable routes will be apparent to one of skill in the art. Any inducing or regulating agent may be delivered by the same route, orally, or by another suitable route.

The invention further provides an antibody construct as described herein labeled with a detectable label. The label may be any suitable label which allows the polypeptide to be detected. Suitable labels include radioisotopes, e.g., 125I, enzymes, and linkers such as biotin. Labeled constructs of the invention may be used in diagnostic procedures such as immunoassays in order to determine the amount of an antibody construct of the invention in a sample. Labeled antibody constructs of the invention may also be used in serological or cell mediated immune assays to said polypeptides in animals and humans using standard protocols. A labeled construct of the invention thereof may also be fixed to a solid phase, for example the surface of an immunoassay well or dipstick. Such labeled and/or immobilized constructs may be packaged into kits in a suitable container along with suitable reagents, controls, instructions and the like.

The following examples are illustrative of the invention and are not limiting.

EXAMPLE 1

Generation of Feline and Canine Optimized Anti-GnRH Antibodies

Murine hybridoma cell line USASK/DSIL-LHRH-A1 [ATCC Accession Number HB-9094, 10801 University Boulevard Manassas, Va. 20110] was selected as an antibody source given the demonstrated capacity of this IgG1 monoclonal antibody to inhibit GnRH signaling in vivo. Extraction of total cellular RNA, cDNA synthesis, and amplification and sequencing of heavy and light chain variable regions has been performed.

Variable Light (VL) Coding Region, SEQ ID NO: 7:

CAAATTGTTCTCACCCAGTCTCCAGCCATCATGTCTGCATCTCCAGGGGA

GAAGGTCACCATAACCTGCAGTGCCACTCAAGTGTAAGTTACATACACTG

GTTCCAGCAGAAGCCAGGCACTTCTCCCAAACTCTGGATTTATAGCACAT

CCAACCTGGCTTCTGGAGTCCCTGTTCGCTTCAGTGGCAGTGGATCTGGG

ACCTCTTACTCTCTCACAATCAGCCGAATGGAGGCTGAAGATGCTGCCAC

TTATTACTGCCAGCAAAGGAGTAGTTACCCACCCACGTTCGGAGGGGGGA

CCAACTGGAAATAAAACGVHCAGATCCAGTTGGTGCAGTCTGGACCTGAA

CTGAAGAAGCCTGGAGAGACAGTCAAGATCTCCTGCAAGGCTTCTGGATA

TCCCTTCACAAACTATGGAATGAACTGGGTGAAGCAGGCTCCAGGAAAGG

GTTTAAAGTGGATGGGCTGGATAAACACCTACACTGGAGAGCCAGCATGT

GCTGATGACTTCAGGGGACGGTTTGCCATCTCTTTGGAAACCTCCGCCAG

ACTGCCTATTTGCAGATCAACAACCTCATAAATGAGGACACGGCAACATA

TTTCTGTGCAAGAACGGGGGTGGTAGGTACAACTATGGTATGGACTATT

GGGGTCAAGGAACCTCAGTCACCGTCTCCTCA

These VL and VH amino acid sequences were analyzed and mutations from germline sequences that occur outside the CDRs (3 in the heavy chain variable region, one in VL) were identified. These mutations are relative to the corresponding germline alleles IGKV4-57*01 (light chain) and IGHV9-3-1*01 (heavy) are marked with parenthesis in the following translated sequences.

VL Amino Acid Sequence, using single letter codes, SEQ ID NO:6:

QIVLTQSPAIMSASPGEKVTITCSATSSVSYIHWFQQKPGTSPKLWIYST

SNLASGVP(V)RFSGSGSGTSYSLTISRMEAEDAATYYCQQRSSYPPTF

GGGTKLEIKR

Variable Heavy (VH) Coding Region, SEQ ID NO: 13:

```
CAGATCCAGTTGGTGCAGTCTGGACCTGAACTGAAGAAGCCTGGAGAGAC

AGTCAAGATCTCCTGCAAGGCTTCTGGATATCCCTTCACAAACTATGGAA

TGAACTGGGTGAAGCAGGCTCCAGGAAAGGGTTTAAAGTGGATGGCTGG

ATAAACACCTACACTGGAGAGCCAGCATGTGCTGATGACTTCAGGGGACG

GTTTGCCATCTCTTTGGAAACCTCCGCCAGAACTGCCTATTTGCAGATCA

ACAACCTCATAAATGAGGACACGGCAACATATTTCTGTGCAAGAACGGGG

GGTGGTAGGTACAACTATGGTATGGACTATTGGGGTCAAGGAACCTCAGT

CACCGTCTCCTCA
```

VH Amino Acid Sequence, using single letter codes, SEQ ID NO: 12:

```
QIQLVQSGPELKKPGETVKISCKASGYPFTNYGMNWVKQAPGKGLKWMGW

INTYTGEPACADDFRGRFA(I)SLETSA(R)TAYLQINNL(I)NEDTAT

YFCARTGGGRYNYGMDYWGQGTSVTVSS
```

The initial chimeric version of the anti-GnRH antibody was generated by fusing murine variable region sequences with human IgG1 heavy chain and kappa light chain constant domains. The sequences of the murine anti-GnRH variable regions were obtained by PCR amplification from total cDNA of the mouse hybridoma cell line USASK/DSIL-LHRH-A1 (ATCC, Manassas, Va.) using primers specific to antibody constant regions and variable region leader sequences (LakePharma, Belmont, Calif.). After optimizing the codon usage in the variable region sequences to mimic that of other highly expressed antibody constructs, these sequences were synthesized (Life Technologies, Grand Island, N.Y.) and cloned into a vector containing the human IgG1 and kappa constant domains, resulting in two open reading frames encoding full length chimeric heavy and light chains. The expression construct contained a CMV promoter upstream of the heavy chain sequence, an encephalomyocarditis virus internal ribosomal entry site sequence separating the heavy and light chain sequences, and a 3' SV40 polyadenylation sequence. The entire expression construct was flanked by the AAV2 inverted terminal repeats.

Expression of the chimeric antibody construct was evaluated by lipofectamine (Life Technologies, Grand Island, N.Y.) mediated transient transfection of 293 HEK cells. Supernatant was harvested eight hours after transfection and passed through a 0.2 µm syringe filter (Corning, Corning, N.Y.). Filtered supernatant was evaluated for total antibody expression and GnRH binding activity using protein A and GnRH ELISAs, respectively. Polystyrene ELISA plates (Corning) were coated overnight at room temperature with protein A (5 µg/mL, Sigma Aldrich, St Louis, Mo.) or GnRH peptide (1 µg/mL, Peptides International, Louisville, Ky.) in phosphate buffered saline. Plates were washed five times with PBS containing 0.05% tween 20 (Sigma), then blocked for one hour at room temperature with 1% bovine serum albumin in PBS. Filtered supernatant serially diluted two-fold in PBS was incubated in blocked wells for one hour. Plates were washed five times, then incubated for one hour with a biotinylated goat anti-human IgG1 antibody (Jackson ImmunoResearch, West Grove, Pa.) diluted 1:10,000 in blocking solution. Plates were then washed, incubated with streptavidin-HRP (Abcam, Cambridge, Mass.) diluted 1:30,000 in blocking solution for one hour, washed again, and developed with TMB substrate (Sigma). The reaction was stopped after 20 minutes by the addition of 2 N sulfuric acid. Absorbance was measured at 405 nm, with a reading at 540 nm subtracted as background. Protein A ELISA indicated an antibody concentration of 60 ng/mL in culture supernatant, based on a standard curve generated using a purified human IgG1 monoclonal antibody (B12, Immune Technology Corp, New York, N.Y.). The GnRH ELISA showed a strong binding signal in the supernatant from transfected but not mock transfected cells. To verify the specificity of binding and to calculate the dissociation constant of the chimeric antibody, the GnRH ELISA was repeated using 10-fold diluted supernatant pre-incubated overnight with various concentrations of GnRH peptide, according to the method of Friguet et al., 1985. The fraction of antibody binding sites occupied by GnRH was calculated using the method of Stevens, 1987. Plotting the fraction of binding sites occupied against GnRH peptide concentration produced a sigmoidal curve (FIG. 1). A curve was fitted to the data by nonlinear regression using GraphPad Prism (GraphPad Software, San Diego Calif. USA), and the Kd was calculated as 3.9 nM.

Following confirmation of antibody expression and GnRH binding activity, the construct was packaged in an AAV serotype 8 vector and purified as previously described Lock M, et al. Rapid, simple, and versatile manufacturing of recombinant adeno-associated viral vectors at scale. *Hum Gene Ther.* 2010; 21(10): 1259-1271.

Figure 2:
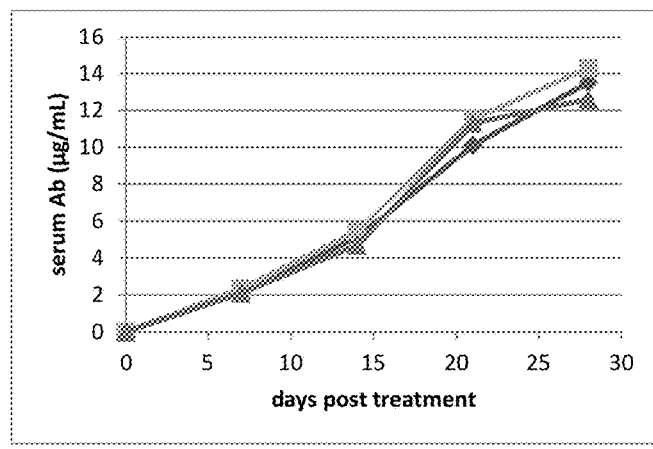
FIG. 2 shows serum concentration of the GnRH specific antibody in three C57BL/6 RAG mice following intramuscular injection of $1 \times 10^{11}$ GC AAV8-Ab.GnRH.
Figure 3:
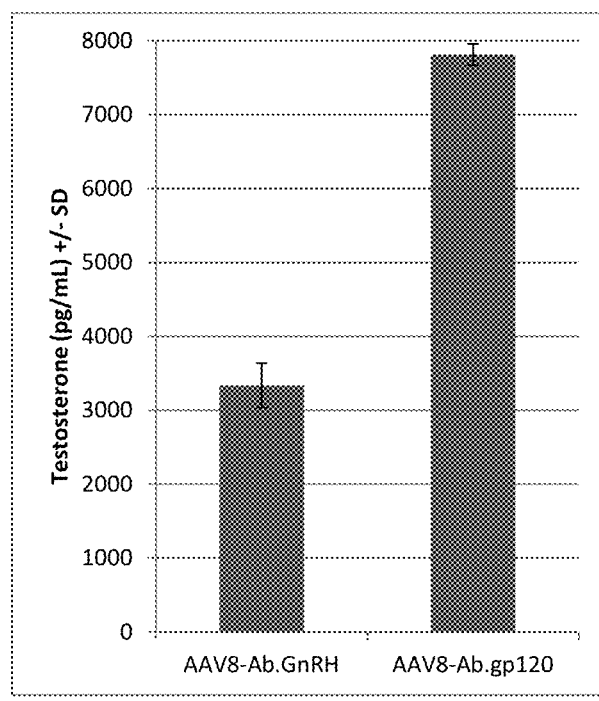
FIG. 3 shows the testosterone concentration in pooled serum from three male mice 28 days following treatment with AAV8-Ab.GnRH. Contro CDRs from the other domain, contribute to the formation of the antigen binding site (GnRH). CDRs and framework regions of antibodies may be determined by reference to Kabat et al ("Sequences of proteins of immunological interest" US Dept. of Health and Human Services, US Government Printing Office, 1987) (based on sequence variability and the most commonly used system), Chothia (numbering system based on the location of the structural loop region), or the AbM numbering system (compromise between Kabat and Chothia, used by Oxford Molecule's AbM antibody modeling software).

An initial proof of concept study was carried out with 3 male C57BL/6 RAG knockout mice (Jackson Laboratory, Bar Harbor, Me.) treated with a single intramuscular injection of $1 \times 10^{11}$ genome copies (gc) of the AAV 8 vector expressing the chimeric anti-GnRH antibody (AAV8-CMV-Ab.GnRH). Three additional male C57BL/6 RAG knockout mice treated with an equivalent dose of an AAV8 vector (AAV8-Ab.gp120) expressing an HIV specific antibody served as controls. Serum concentration of the antibody was measured weekly by protein A ELISA (FIG. 2). Serum testosterone was measured at day 28 using a commercial immunoassay (Cayman Chemical, Ann Arbor, Mich.). Pooled serum testosterone was more than two fold higher in the animals that received the control vector than animals treated with the GnRH specific vector (FIG. 3), indicating suppression of the hypothalamic-pituitary-gonadal axis.

Figure 4:
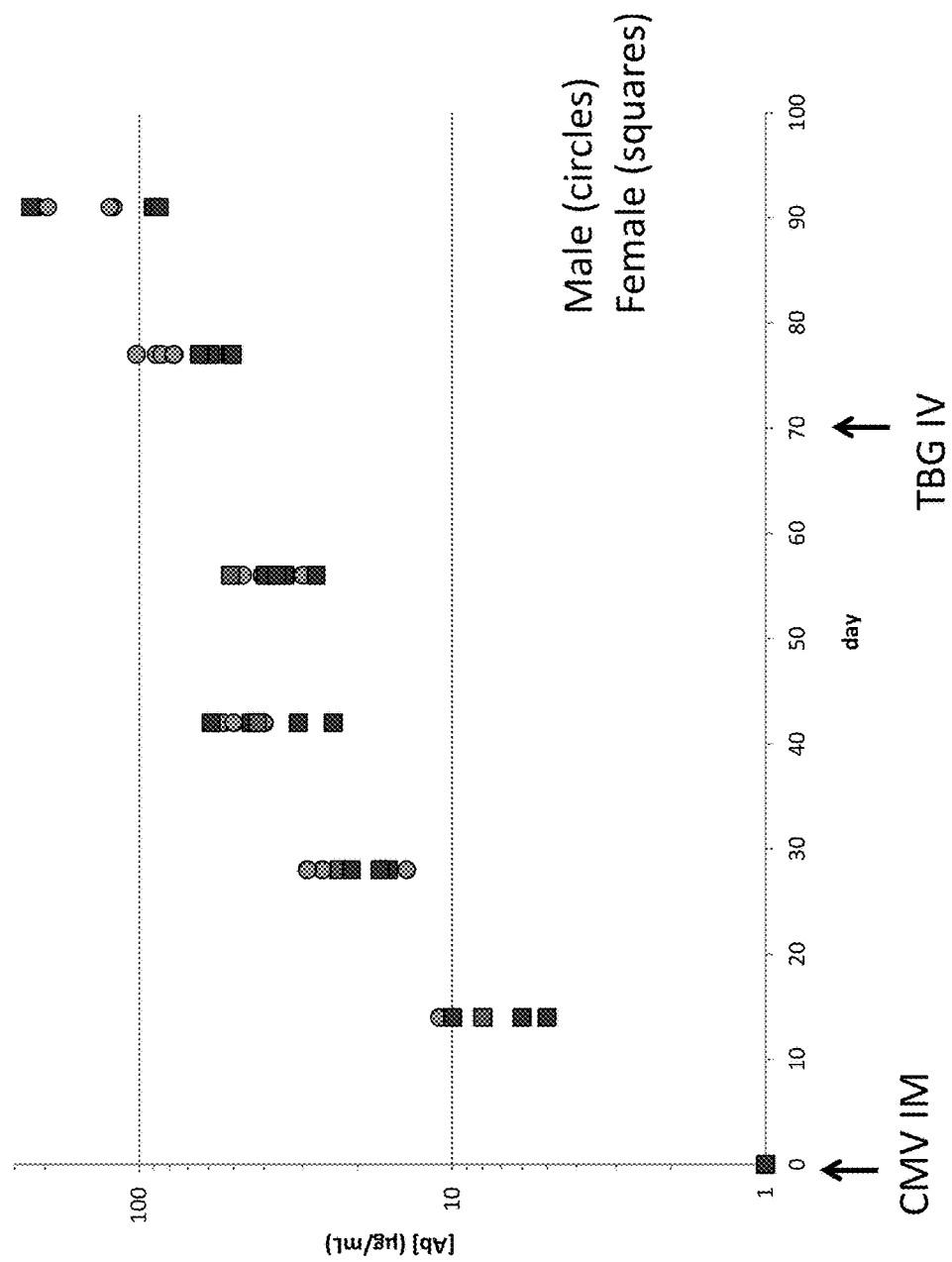

A second study was performed with 6 male and 6 female C57BL/6 RAG knockout mice (Jackson Laboratory, Bar Harbor, Me.). In addition to the previously described vector employing a CMV promoter, a second vector was developed with the CMV promoter replaced by a liver specific thyroid hormone binding globulin (TBG) promoter. All mice were treated with the original CMV vector (AAV8-CMV-Ab.GnRH, $1 \times 10^{11}$ gc) by intramuscular injection, followed by intravenous injection of the TBG promoter bearing vector (AAV8-TBG-Ab.GnRH, $1 \times 10^{11}$ gc) 70 days after the initial injection. Serum antibody concentrations were measured by protein A ELISA as described above (FIG. 4). Serum testosterone was measured in individual male mice on day 14 and 21 following injection of the second vector. Control animals receiving a vector expressing an HIV specific antibody (AAV8-Ab.gp120) exhibited normal physiologic fluctuations in serum testosterone (FIG. 5a), whereas animals treated with the GnRH specific vector exhibited persistently suppressed serum testosterone (FIG. 5b).

EXAMPLE 2

Development of Canine and Feline Anti-GnRH Antibodies by CDR Grafting

To select canine and feline variable region frameworks, variable region amino acid sequences with significant homology to the murine anti-GnRH variable region were identified by BLAST (http://blast.ncbi.nlm.nih.gov). The feline heavy and light chain variable region amino acid sequences selected were GenBank# BAJ83699.1 and AAF09245.1, respectively. The canine heavy and light chain variable region sequences selected were ABN11154.1 and Swiss-Prot # P01618.1. The complementarity determining regions were identified in the murine, canine and feline sequences according to the guidelines of Martin et al. (www.bioinf.org.uk/abs/#cdrid). The murine complementarity determining regions, as well as the 3 heavy chain and 1 light chain somatic mutations identified in the murine sequence, were transferred onto the canine and feline acceptor sequences. The constant domains selected were the feline kappa light (GenBank# AAF09245.1), canine kappa light (Ensembl ID: Enscafp00000010929), feline IgG heavy allele A (GenBank# BAA32229.1), and canine IgGA heavy (GenBank# AAL35301.1). The entire antibody amino acid sequences were backtranslated using codon preferences of highly expressed antibody constructs. These sequences were commercially synthesized (Life Technologies, Grand Island, N.Y.) and cloned into the expression vector used for the initial chimeric constructs.

Complete canine antibody heavy chain amino acid sequence (variable heavy sequence (SEQ ID NO: 14) fused to antibody constant regions (highlighted portions), SEQ ID NO: 28

EVQLVESGGDLVKPAGSLRLSCVASGYPFTNYGMNWVRQAPGKGLQWVAW

INTYTGEPACADDFRGRFTISRDNAKRTLYLQMNSLIAEDTAVYYCAKTG

GGRYNYGMDYWGHGTSLFVSSASTTAPSVFPLAPSCGSTSGSTVALACLV

SGYFPEPVTVSWNSGSLTSGVHTFPSVLQSSGLHSLSSMVTVPSSRWPSE

TFTCNVVHPASNTKVDKPVFNECRCTDTPPCPVPEPLGGPSVLIFPPKPK

DILRITRTPEVTCVVLDLGREDPEVQISWFVDGKEVHTAKTQSREQQFNG

TVRVVSVLPIEHQDWLTGKEFKCRVNHIDLPSPIERTISKARGRAHKPSV

YVLPPSPKELSSSDTVSITCLIKDFYPPDIDVEWQSNGQQEPERKHRMTP

PQLDEDGSYFLYSKLSVDKSRWQQGDPFTCAVMHETLQNHYTDLSLSHSP

GK

Complete feline antibody heavy chain amino acid sequence (variable heavy sequence (SEQ ID NO: 16) fused to antibody constant regions (highlighted portions), SEQ ID NO: 32:

DVQLMESGGDLVKPGGSLRLTCVASGYPFTNYGMNWVRQAPGKGLQWVAW

INTYTGEPACADDFRGRFTISRDNAKRTLYLQMNSLITEDTATYYCTRTG

GGRYNYGMDYWGQGALVTVSSASTTAPSVFPLAPSCGTTSGATVALACLV

LGYFPEPVTVSWNSGALTSGVHTFPAVLQASGLYSLSSMVTVPSSRWLSD

TFTCNVAHPPSNTKVDKTVRKTDHPPGPKPCDCPKCPPPEMLGGPSIFIF

PPKPKDTLSISRTPEVTCLVVDLGPDDSDVQITWFVDNTQVYTAKTSPRE

EQFNSTYRVVSVLPILHQDWLKGKEFKCKVNSKSLPSPIERTISKAKGQP

HEPQVYVLPPAQEELSRNKVSVTCLIKSFHPPDIAVEWEITGQPEPENNY

RTTPPQLDSDGTYFVYSKLSVDRSHWQRGNTYTCSVSHEALHSHHTQKSL

TQSPGK

Complete canine antibody light chain amino acid sequence (variable light sequence (SEQ ID NO: 8) fused to antibody constant regions (highlighted portion), SEQ ID NO: 30:

DIVMTQTPLSLSVSPGEPASISCSATSSVSYIHWYLQKAGQSPRLLPEST

SNLASGVPVRFSGSGSGTDFTLRIGRVEAEDAGIYYCQQRSSYPPTFGQG

TRLEVRRNDAQPAVYLFQPSPDQLHTGSASVVCLLNSFYPKDINVKWKVD

GVIQDTGIQESVTEQDKDSTYSLSSTLTMSSTEYLSHELYSCEITHKSLP

STLIKSFQRSEC

Complete feline antibody light chain amino acid sequence (variable light sequence (SEQ ID NO: 10) fused to antibody constant regions (highlighted portion), SEQ ID NO: 34

DIVMTQTPLSLSVTPGEPASISCSATSSVSYIHWYLQKPGQSPRRLIYST

SNLASGVPVRFSGSGSGTDFTLRISRVEADDVGVYYCQQRSSYPPTFGPG

TKLEIKRSDAQPSVFLFQPSLDELHTGSASIVCILNDFYPKEVNVKWKVD

GVVQNKGIQESTTEQNSKDSTYSLSSTLTMSSTEYQSHEKFSCEVTHKSL

ASTLVKSFNRSECQRE

Canine antibody heavy chain nucleotide sequence, SEQ ID NO: 27:

gaggtgcagctggtggagagcggcggggatctggtcaagcctgccggcag cctgagactgagctgcgtggcaagcggctacccttcacaaattatggca tgaactgggtgcgacaggcccctggcaagggcctgcagtgggtggcctgg ataaacacctacaccggggaaccagcatgtgcagatgacttcagaggccg cttcaccatatctcgagacaatgctaagcggaccctgtatctgcagatga actcactgattgcagaggacacagcagtgtactactgtgccaagacagga ggagggcgctacaactatggcatggactactggggccacggaacgagcct gtttgtctcatctgcgtcgaccacagcccctctgtgttcccctggccc cttcctgtgggtcaacctctggcagcacagtggccctggcgtgtcttgtg tctggctacttccctgaacctgtgacagtcagctggaacagcggaagcct gacctctggagtgcacaccttccccagtgtcctgcaaagctcaggcctgc acagcctgtcaagtatggtgacagtgcccagtagcaggtggccttctgaa acctttacctgcaacgtggtgcaccctgcatccaacaccaaagtggataa gcctgttttcaatgagtgcagatgcacagatacacctccctgccctgtgc ctgagcctctgggaggaccatcagtcctgatcttccctccaaagcctaag -continued gatatcctgcggatcaccagaaccccgaggtcacctgtgtcgtcctgga tctgggccgggaagatcctgaagtgcagattagctggtttgtggacggca aggaagtgcacacagctaagacccaatcccgggagcagcagttcaatggc acctaccgggtggtctctgtcctgccatcgagcaccaagattggctgac aggcaaagagtttaagtgccgagtcaaccacatagatcttccctcccta ttgagcggaccatctccaaggcacgggggcgagcgcacaaaccctctgtc tatgtgctgcctccctctcccaaagaattgagctctagcgatacagtgtc aatcacctgcctgatcaaggacttctaccccctgacattgatgttgaat ggcaatcaaatgggcagcaagaaccagagagaaaacacagaatgacccct ccacagctggatgaggacgggtcctactttctgtactctaaactttccgt ggacaagagcagatggcagcagggagaccattcacctgtgcggtcatgca cgagacactgcaaaaccactacacagatctgtccttgagccactcacctg gcaag Canine antibody light chain nucleotide sequence, SEQ ID NO: 29:

GATATAGTGATGACCCAAACCCCTCTAAGCCTATCTGTCTCCCCTGGGGA

GCCGGCGAGTATCAGCTGCAGCGCCACCAGCAGCGTGTCATATATCCACT

GGTACCTGCAAAAGGCTGGACAGTCCCCTAGACTTCTGCCCGAAAGCACA

TCTAACCTGGCCAGCGGGGTCCCTGTGAGGTTTAGTGGGAGTGGGAGTGG

CACCGATTTCACCCTCCGAATTGGAAGGGTGGAGGCCGAAGATGCTGGAA

TCTATTACTGTCAGCAAAGAAGCAGCTACCCCCCTACCTTCGGGCAGGGC

ACCAGACTTGAGGTCCGCAGGAATGATGCTCAGCCTGCTGTGTACCTTTT

TCAACCAAGCCCTGACCAACTGCATACCGGCAGTGCCTCTGTGGTCTGCC

TGCTTAATAGCTTCTATCCCAAGGACATTAATGTGAAGTGGAAGGTTGAC

GGCGTGATACAGGATACCGGAATTCAGGAAAGTGTGACAGAACAAGATAA

GGATAGCACCTATAGCCTGTCTAGCACCCTCACCATGAGCAGCACAGAGT

ACTTGAGTCATGAGCTGTATAGCTGTGAGATTACCCACAAGAGTCTGCCA

Feline antibody heavy chain nucleotide sequence, SEQ ID NO: 31:

gacgtgcagctgatggagtctgggggcgacctagtcaagcctgggggtc cctgcggcttacgtgtgtggcaagtgggtacccttcaccaactatggaa tgaactgggtcagacaggcccctggaaaaggcctgcagtgggtggcctgg atcaacacctatacaggagaacctgcctgtgcagatgactttagaggcg attcaccatttcaagagataacgcgaagcgaaccttgtacttacagatga actccctgatcacagaagacacagcaacctactactgtacccggacagga gggggccgctacaactatggcatggactactgggggcaaggagcactggt gacagtctcatctgcgtcgaccacagcccctctgtgttcccctggccc cttcttgtggaaccacctctggagcgacagtggctctggcgtgccttgtc ctgggggtacttccctgaacctgtgaccgtcagctggaactccggagcact gacatctggagtgcacacctttcctgcggtcctgcaagcttccggcctgt actcactgtccagcatggtgactgtgccttcttcaagatggctgtctgac acgttcacctgcaatgtggcgcaccctccttcaaacacaaaggtcgataa gaccgtgagaaagacagaccaccccctggcccaaagccctgcgactgtc ctaagtgccccctcctgaaatgctgggcggcccagcatcttcatattc cccctaagcccaaagacaccttgagtatctctcgaacaccagaagtcac ctgcctggtggtggacctaggccctgatgactctgatgtgcaaataacct ggttcgtggacaacacccaggtgtacaccgccaaaacctccccaagagag gagcagttcaactccacctatcgggtcgttagtgtgctgcccattctgca ccaagactggctgaaaggcaaggagttcaagtgcaaggtcaatagcaaat cactgcctctcccattgaaagaaccattagcaaggccaagggacagccc cacgaacctcaggtgtatgtgctgccacctgcccaggaagagctcagccg caacaaggtctctgtgacctgcctgatcaagtccttccaccctcctgaca tagcagtggagtgggaaataacaggacagcctgagcctgaaaacaactac cgcaccacccctcccaactggactccgatggaacctactttgtctactc taagctgtctgtggatcgaagccactggcaaggggcaacacctacacct gctctgtcagccacgaagccctgcacagccaccacacccaaaagtccctg acccagagccccggaaag Feline antibody light chain nucleotide sequence, SEQ ID NO: 33:

GACATCGTGATGACCCAAACCCCTCTGAGCCTGTCCGTCACCCCCGGGGA

GCCCGCCAGCATAAGCTGCTCCGCTACCAGCTCCGTTAGCTACATTCACT

GGTATCTGCAAAAGCCTGGCCAGAGCCCTAGGCGACTGATCTATAGCACC

TCCAACCTGGCCTCTGGTGTGCCAGTGCGCTTCTCTGGGTCTGGCAGCGG

GACCGACTTTACCCTGAGGATCTCCAGAGTGGAGGCTGATGATGTGGGGG

TGTACTACTGCCAGCAGAGGAGCAGCTATCCTCCTACCTTTGGCCCCGGC

ACCAAGCTGGAGATAAAGAGGAGTGATGCCCAGCCCAGCGTGTTTCTGTT

CCAACCTTCTCTGGATGAGCTGCACACCGGGAGCGCCTCTATAGTGTGTA

TTCTGAATGATTTCTATCCCAAAGAAGTTAATGTCAAGTGGAAGGTGGAT

GGGGTGGTCCAGAACAAGGGCATCCAGGAAAGCACGACCGAACAGAACTC

CAAGGACTCCACATATTCTCTGAGTAGTACCCTGACCATGAGTAGCACCG

AATACCAGAGTCACGAGAAATTCAGCTGCGAGGTGACCCACAAGAGCTTG

GCCAGCACCCTAGTGAAGAGCTTTAACCGAAGCGAGTGCCAGCGAGAA

| Sequence Listing Free Text | |
|---|---|
| SEQ ID NO: | <213> Artificial Sequence <220> |
| 18 | <223> Antibody CDR VH1 |
| 19 | <223> Antibody CDR VH1 |
| 20 | <223> Antibody CDR VH1 |
| 21 | <223> Antibody CDR VH1 |
| 22 | <223> Antibody CDR VH2 |
| 23 | <223> Antibody CDR VH3 |
| 24 | <223> Antibody CDR VL1 |

Sequence Listing Free Text

| SEQ ID NO: | <213> Artificial Sequence<br><220> |
|---|---|
| 25 | <223> Antibody CDR VL2 |
| 26 | <223> Antibody CDR VL3 |
| 27 | <223> Full length antibody heavy chain (HC) with canine CDR coding sequence |
| 28 | <223> Synthetic Construct |
| 29 | <223> Full Length antibody light chain coding with canine CDR sequence |
| 30 | <223> Synthetic Construct |
| 31 | <223> Full length antibody heavy chain with feline CDR |
| 32 | <223> Synthetic Construct |
| 33 | <223> Full-length antibody light chain with feline CDR |
| 34 | <223> Synthetic Construct |

Applicant hereby incorporates by reference the Sequence Listing material filed in electronic form herewith. This file is labeled UPN-Z6451PCT.ST25.txt.

All publications, patents, and patent applications cited in this application, as well as U.S. Patent Application No. 61/785,547, filed Mar. 14, 2013 and U.S. Patent Application No. 61/707,900, filed Sep. 29, 2012, are hereby incorporated by reference in their entireties as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

The invention claimed is:

1. A composition useful for non-surgical sterilization of non-human mammals, said composition comprising an adeno-associated virus (AAV) vector having an AAV capsid having packaged therein nucleic acid sequences comprising an AAV 5' inverted terminal repeat (ITR), a sequence encoding a polypeptide which comprises a functional portion of an antibody which specifically binds and neutralizes gonadotropin releasing hormone (GnRH), wherein the functional portion of the antibody has a heavy chain variable amino acid sequence of:

(a) murine, SEQ ID NO: 12: QIQLVQSGPELKKPGETVKISCK
ASGYPFT-NYGMNWVKQAPGKGLKWMGWINTYTGEPACADD
FRGRFA(I)SLETSA(R)TAYLQINNL(I)NEDTATYFCARTGGGRYN
YGMDYWGQGTSVTVSS;

-continued
(b) canine, SEQ ID NO: 14: EVQLVESGGDLVKPAGSLRLS
CVA-SGYPFTNYGMNWVRQAPGKGLQWVAWINTYTGEPA
CADDFRGRFTISRDNAKRTLYLQMNSLIAEDTAVYYCAKTGG
GRYNYGMDYWGHGTSLFVSS; and (c) feline, SEQ ID NO: 16:
DVQLMESGGDLVKPGGSLRLTCVAS-
GYPFTNYGMNWVRQAPGKGLQWVAWINTYTGEPACADDFRG
RFTISRDNAKRTLYLQMNSLITEDTATYYCTRTGGGRYNYGMDYW
GQGALVTVSS, or a sequence having about 97% to about 99% identity with one of (a) to (c).

2. The composition according to claim 1, wherein the polypeptide is an anti-GnRH antibody, immunoadhesin, a functional portion of the antibody which neutralizes GnRH, or a fusion protein comprising a functional portion of the antibody which neutralizes GnRH.

3. The composition according to claim 2, wherein the functional portion of the antibody which neutralizes GnRH is selected from a Fab, Fab', scFv, or a heavy chain variable domain.

4. The composition according to claim 1, wherein:

(a) the heavy chian vari-
able amino acid sequence is
the murine sequence and is encoded by: SEQ ID NO: 13:
CAGATCCAGTTGGTGCAGTCTGGACCTGAACTGAAGAAGCCTGGAGAGAC
AGTCAAGATCTCCTGCAAGGCTTCTGGATATCCCTTCACAAACTATGGAA
TGAACTGGGTGAAGCAGGCTCCAGGAAAGGGTTTAAAGTGGATGGGCTGG
ATAAACACCTACACTGGAGAGCCAGCATGTGCTGATGACTTCAGGGGACG
GTTTGCCATCTCTTTGGAAACCTCCGCCAGAACTGCCTATTTGCAGATCA
ACAACCTCATAAATGAGGACACGGCAACATATTTCTGTGCAAGAACGGGG
GGTGGTAGGTACAACTATGGTATGGACTATTGGGGTCAAGGAACCTCAGT
CACCGTCTCCTCA, or (b) the heavy chain vari-
able amino acid sequence is
the canine sequence and is encoded by: SEQ ID NO: 15:
gaggtgcagctggtggagagcggcggggatctggtcaagcctgccggcag
cctgagactgagctgcgtggcaagcggctacccctcaccaaatatggca
tgaactgggtgcgacaggcccctggcaaggcctgcagtgggtggcctgg
ataaacacctacaccggggaaccagcatgtgcagatgacttcagaggccg
cttcaccatatctgagacaatgctaagcggaccctgtatctgcagatga
actcactgattgcagaggacacagcagtgtactactgtgccaagacagga
ggagggcgctacaactatggcatggactactggggcacggaacgagcct
gtttgtctcatctgcgtcgaccacagcccctctgtgttcccctggccc
cttcctgtgggtcaacctaggcagcacagtggccctggcgtgtcttgtgt
ctggctacttccctgaacctgtgacagtcagctggaacagcggaagcctg
acctctggagtgcacaccttcccagtgtcctgcaaagctcaggcctgca
cagcctgtcaagtatggtgacagtgcccagtagcaggtggccttctgaaa
cctttacctgcaacgtggtgcaccctgcatccaacaccaaagtggataag
cctgttttcaatgagtgcagatgcacagatacacctccctgccctgtgcc
tgagcctctgggaggaccatcagtcctgatcttccctccaaagcctaagg
atatcctgcggatcaccagaacccccgaggtcacctgtgtcgtcctggat
ctgggccgggaagatcctgaagtgcagattagctggtttgtggacggcaa
ggaagtgcacacagctaagacccaatcccgggagcagcagttcaatggca
cctaccgggtggtctctgtcctgcccatcgagcaccaagattggctgaca
ggcaaagagtttaagtgccgagtcaaccacatagatcttcctctcccctat
tgagcggaccatctccaaggcacggggcgagcgcacaaaccctctgtct
atgtgctgcctccctctcccaaagaattgagctctagcgatacagtgtca
atcacctgcctgatcaaggacttctcaccccctgacattgatgttgaatg
gcaatcaaatgggcagcaagaaccagagagaaaacacagaatgacccctc
cacagctggatgaggacgggtcctactttctgtactctaaactttccgtg
gacaagagcagatggcagcagggagaccattcacctgtgcggtcatgcac
gagacactgcaaaaccactacacagatctgtccttgagccactcacctgg
caag;

or (c) the heavy chain vari-
able amino acid sequence
is the feline sequence and is encoded by:
SEQ ID NO: 17:
gacgtgcagctgatggagtctgggggcgacctagtcaagcctgggggtc
cctgcggcttacgtgtgtggcaagtgggtaccccttcaccaactatgga
tgaactgggtcagacaggcccctggaaaaggcctgcagtgggtggcctgg
atcaacacctatacaggagaacctgcctgtgcagatgactttagaggccg
attcaccatttcaagagataacgcgaagcgaaccttgtacttacagatga
actccctgatcacagaagacacagcaacctactactgtacccggacagga -continued
ggggggccgctacaactatggcatggactactgggggcaaggagcactggt
gacagtctcatctgcgtcgaccacagcccctagtgaccccctggcccct
tcttgtggaaccacctctggagcgacagtggctctggcgtgccttgtcct
ggggtacttccctgaacctgtgaccgtcagctggaactccggagcactga
catctggagtgcacaccttttcctgcggtcctgcaagcttccggcctgtac
tcactgtccagcatggtgactgtgccttcttcaagatggctgtctgacac
gttcacctgcaatgtggcgcaccaccttcaaacacaaaggtcgataagac
cgtgagaaagacagaccaccccctggcccaaagccctgcgactgtccta
agtgccccctcctgaaatgagggcggcccagcatcttcatattccccc
ctaagcccaaagacaccttgagtatctctcgaacaccagaagtcacctgc
ctggtggtggacctaggccctgatgactagatgtgcaaataacctggttc
gtggacaacacccaggtgtacaccgccaaaacctcccaagagaggagca
gttcaactccacctatcgggtcgttagtgtgctgcccattctgcaccaag
actggctgaaaggcaaggagttcaagtgcaaggtcaatagcaaatcactg
ccctatcccattgaaagaaccattagcaaggccaagggacagcccacga
acctcaggtgtatgtgctgccacctgcccaggaagagctcagccgcaaca
aggtctctgtgacctgcctgatcaagtccttccaccctcctgacatagca
gtggagtgggaaataacaggacagcctgagcctgaaaacaactaccgcac
caccccctcccaactggactccgatggaacctactttgtctactctaaga
gtagtggatcgaagccactggcaaaggggcaacacctacacctgctctgt
cagccacgaagccctgcacagccaccacacccaaaagtccctgacccaga
gccccggaaag or a sequence having about 97% to about 99% identity with one of (a) to (c).

5. The composition according to claim 1, wherein the anti-GnRH antibody or functional portion thereof comprises non-canine complementarity determining regions (CDRs) in canine immunoglobulin constant framework regions.

6. The composition according to claim 5, wherein sequences encoding the anti-GnRH antibody or functional portion thereof is optimized for canine delivery.

7. The composition according to claim 1, wherein the antibody is an IgG protein.

8. The composition according to claim 1, wherein the AAV has a capsid which is selected from the group consisting of AAV1, AAV8, and AAV9.

9. A composition useful for non-surgical sterilization of non-human mammals, said composition comprising an adeno-associated virus (AAV) vector having an AAV capsid having packaged therein nucleic acid sequences comprising an AAV 5' inverted terminal repeat (ITR), a sequence encoding a polypeptide which comprises a functional portion of an antibody which specifically binds and neutralizes gonadotropin releasing hormone (GnRH), wherein the functional portion of the antibody has a light chain variable amino acid sequence of:

(a) murine, SEQ ID NO: 6:
QIVLTQSPAIMSASPGEKVTITCSATSSVSYIHWFQQKPGTSPKLWIYST
SNLASGVP(V)RFSGSGSGTSYSLTISRMEAEDAATYYCQQRSSYPPTFG
GGTKLEIKR; or (b) canine, SEQ ID NO: 8:
DIVMTQTPLSLSVSPGEPASISCSATSSVSYIHWYLQKAGQSPRLLPEST
SNLASGVPVRFSGSGSGTDFTLRIGRVEAEDAGIYYCQQRSSYPPTFGQG
TRLEVRR, or (c) feline, SEQ ID NO: 10:
DIVMTQTPLSLSVTPGEPASISCSATSSVSYIHWYLQKPGQSPRRLIYST
SNLASGVPVRFSGSGSGTDFTLRISRVEADDVGVYYCQQRSSYPPTFGPG
TKLEIKR;

or a sequence having about 97% to about 99% identity with one of (a) to (c).

10. The composition according to claim 9, wherein:

(a) the light chain vari-
able amino acid sequence is
the murine sequence and is enclosed by:
SEQ ID NO: 7:
CAAATTGTTCTCACCCAGTCTCCAGCCATCATGTCTGCATCTCCAGGGGA
GAAGGTCACCATAACCTGCAGTGCCACTCAAGTGTAAGTTACATACACTG
GTTCCAGCAGAAGCCAGGCACTTCTCCCAAACTCTGGATTTATAGCACAT -continued

```
CCAACCTGGCTTCTGGAGTCCCTGTTCGCTTCAGTGGCAGTGGATCTGGG
ACCTCTTACTCTCTCACAATCAGCCGAATGGAGGCTGAAGATGCTGCCAC
TTATTACTGCCAGCAAAGGAGTAGTTACCCACCCACGTTCGGAGGGGGA
CCAACTGGAAATAAAACGVHCAGATCCAGTTGGTGCAGTCTGGACCTGAA
CTGAAGAAGCCTGGAGAGACAGTCAAGATCTCCTGCAAGGCTTCTGGATA
TCCCTTCACAAACTATGGAATGAACTGGGTGAAGCAGGCTCCAGGAAAGG
GTTTAAAGTGGATGGGCTGGATAAACACCTACACTGGAGAGCCAGCATGT
GCTGATGACTTCAGGGGACGGTTTGCCATCTCTTTGGAAACCTCCGCCAG
ACTGCCTATTTGCAGATCAACAACCTCATAAATGAGGACACGGCAACATA
TTTCTGTGCAAGAACGGGGGGTGGTAGGTACAACTATGGTATGGACTATT
GGGGTCAAGGAACCTCAGTCACCGTCTCCTCA, or
```

(b) the light chain vari-
able amino acid sequence is
the canine sequence and is encoded by:
SEQ ID NO: 9:
```
GATATAGTGATGACCCAAACCCCTCTAAGCCTATCTGTCTCCCCTGGGGA
GCCGGCGAGTATCAGCTGCAGCGCCACCAGCAGCGTGTCATATATCCACT
GGTACCTGCAAAAGGCTGGACAGTCCCCTAGACTTCTGCCCGAAAGCACA
TCTAACCTGGCCAGCGGGGTCCCTGTGAGGTTTAGTGGGAGTTAGCCTGT
CTAGCACCCTCACCATGAGCAGCACAGAGTACTTGAGTCATGAGCTGTAT
AGCTGTGAGATTACCCACAAGAGTCTGCCAAGCACCCTTATAAAAAGTTT
CCAGCGATCTGAGTGT; or
```

(c) the light chain vari-
able amino acid sequence is
the feline sequence and is encoded by: SEQ ID NO: 11:
```
GACATCGTGATGACCCAAACCCCTCTGAGCCTGTCCGTCACCCCCGGGGA
GCCCGCCAGCATAAGCTGCTCCGCTACCAGCTCCGTTAGCTACATTCACT
GGTATCTGCAAAAGCCTGGCCAGAGCCCTAGGCGACTGATCTATAGCACC
TCCAACCTGGCCTCTGGTGTGCCAGTGCGCTTCTCTGGGTCTGGCAGCGG
GACCGACTTTACCCTGAGGATCTCCAGAGTGGAGGCTGATGATGTGGGGG
TGTACTACTGCCAGCAGAGGAGCAGCTATCCTCCTACCTTTGGCCCCGGC
ACCAAGCTGGAGATAAAGAGGAGTGATGCCCAGCCCAGCGTGTTTCTGTT
CCAACCTTCTCTGGATGAGCTGCACACCGGGAGCGCCTCTATAGTGTGTA
TTCTGAATGATTTCTATCCCAAAGAAGTTAATGTCAAGTGGAAGGTGGAT
GGGGTGGTCCAGAACAAGGGCATCCAGGAAAGCACGACCGAACAGAACTC
CAAGGACTCCACATATTCTCTGAGTAGTACCCTGACCATGAGTAGCACCG
AATACCAGAGTCACGAGAAATTCAGCTGCGAGGTGACCCACAAGAGCTTG
GCCAGCACCCTAGTGAAGAGCTTTAACCGAAGCGAGTGCCAGCGAGAA;
``` or a sequence having about 97% to about 99% identity with one of (a) to (c).

11. The composition according to claim 9, wherein the polypeptide is an anti-GnRH antibody, immunoadhesin, a functional portion of the antibody which neutralizes GnRH, or a fusion protein comprising a functional portion of the antibody which neutralizes GnRH.

12. The composition according to claim 11, wherein the functional portion of the antibody which neutralizes GnRH is selected from a Fab, Fab', scFv, or a heavy chain variable domain.

13. The composition according to claim 9, wherein the anti-GnRH antibody or functional portion thereof comprises non-canine complementarity determining regions (CDRs) in canine immunoglobulin constant framework regions.

14. The composition according to claim 13, wherein sequences encoding the anti-GnRH antibody or functional portion thereof is optimized for canine delivery.

15. The composition according to claim 9, wherein the antibody is an IgG protein.

16. The composition according to claim 9, wherein the AAV has a capsid which is selected from the group consisting of AAV1, AAV8, and AAV9.

17. A lyophilized composition comprising an adeno-associated virus (AAV) vector having a composition comprising an adeno-associated virus (AAV) vector having an AAV capsid having packaged therein nucleic acid sequences comprising an AAV 5' inverted terminal repeat (ITR), a sequence encoding a polypeptide which specifically binds gonadotropin releasing hormone (GnRH) under control of regulatory sequences which direct expression of the ligand, and an AAV 3' ITR, wherein the functional portion of the antibody has a heavy chain variable amino acid sequence of:

(a) murine, SEQ ID NO: 12:
QIQLVQSGPELKKPGETVKISCKASGYPFTNYGMNWVKQAPGKGLKWMGW

INTYTGEPACADDFRGRFA(I)SLETSA(R)TAYLQINNL(I)NEDTATY

FCARTGGGRYNYGMDYWGQGTSVTVSS; or (b) canine, SEQ ID NO: 14:
EVQLVESGGDLVKPAGSLRLSCVASGYPFTNYGMNWVRQAPGKGLQWVAW

INTYTGEPACADDFRGRFTISRDNAKRTLYLQMNSLIAEDTAVYYCAKTG

GGRYNYGMDYWGHGTSLFVSS; or (c) feline, SEQ ID NO: 16:
DVQLMESGGDLVKPGGSLRLTCVASGYPFTNYGMNWVRQAPGKGLQWVAW

INTYTGEPACADDFRGRFTISRDNAKRTLYLQMNSLITEDTATYYCTRTG

GGRYNYGMDYWGQGALVTVSS, or a sequence having about 97% to about 99% identity with one of (a) to (c).

18. A reconstituted composition comprising the lyophilized composition according to claim 17 comprising about $10^9$ to about $5 \times 10^{13}$ vector particles per 1 mL aqueous suspension.

19. A lyophilized composition comprising an adeno-associated virus (AAV) vector having a composition comprising an adeno-associated virus (AAV) vector having an AAV capsid having packaged therein nucleic acid sequences comprising an AAV 5' inverted terminal repeat (ITR), a sequence encoding a polypeptide which specifically binds gonadotropin releasing hormone (GnRH) under control of regulatory sequences which direct expression of the ligand, and an AAV 3' ITR, wherein the polypeptide comprises a light chain variable amino acid sequence of:

(a) murine, SEQ ID NO: 6:
QIVLTQSPAIMSASPGEKVTITCSATSSVSYIHWFQQKPGTSPKLWIYST

SNLASGVP(V)RFSGSGSGTSYSLTISRMEAEDAATYYCQQRSSYPPTFG

GGTKLEIKR;

(b) canine, SEQ ID NO: 8:
DIVMTQTPLSLSVSPGEPASISCSATSSVSYIHWYLQKAGQSPRLLPEST

SNLASGVPVRFSGSGSGTDFTLRIGRVEAEDAGIYYCQQRSSYPPTFGQG

TRLEVRR, or (c) feline, SEQ ID NO: 10:
DIVMTQTPLSLSVTPGEPASISCSATSSVSYIHWYLQKPGQSPRRLIYST

SNLASGVPVRFSGSGSGTDFTLRISRVEADDVGVYYCQQRSSYPPTFGPG

TKLEIKR;

or a sequence having about 97% to about 99% identity with one of (a) to (c).

20. A reconstituted composition comprising the lyophilized composition according to claim 19 comprising about $10^9$ to about $5 \times 10^{13}$ vector particles per 1 mL aqueous suspension.

* * * * *